US011094396B2

(12) United States Patent
Uten et al.

(10) Patent No.: US 11,094,396 B2
(45) Date of Patent: Aug. 17, 2021

(54) METHODS FOR FLUORESCENCE DATA CORRECTION

(71) Applicant: UgenTec NV, Hasselt (BE)

(72) Inventors: Wouter Uten, Hasselt (BE); Martin Reijans, Maastricht (NL); Yves Antonius Ozog, Zonhoven (BE)

(73) Assignee: UgenTec NV, Hasselt (BE)

( * ) Notice: Subject to any disclaimer, the term of this patent is extended or adjusted under 35 U.S.C. 154(b) by 310 days.

(21) Appl. No.: 16/138,386

(22) Filed: Sep. 21, 2018

(65) Prior Publication Data

US 2019/0026426 A1 Jan. 24, 2019

Related U.S. Application Data

(63) Continuation-in-part of application No. 15/303,105, filed as application No. PCT/IB2015/052667 on Apr. 13, 2015, now abandoned.

(30) Foreign Application Priority Data

Apr. 11, 2014 (BE) .................................. 2014/0251

(51) Int. Cl.
*G16B 25/00* (2019.01)
*G01N 21/64* (2006.01)
(Continued)

(52) U.S. Cl.
CPC .............. *G16B 25/00* (2019.02); *C12Q 1/68* (2013.01); *C12Q 1/686* (2013.01);
(Continued)

(58) Field of Classification Search
CPC .......... G16B 25/00; C12Q 1/68; C12Q 1/686; G01N 21/6428; G01N 2021/6421;
(Continued)

(56) References Cited

U.S. PATENT DOCUMENTS 6,197,520 B1 3/2001 Wittwer et al.
6,197,850 B1 3/2001 Posada Fernandez et al.
(Continued)

FOREIGN PATENT DOCUMENTS

CN 102235976 A 11/2011
CN 104321635 A 1/2015
(Continued)

OTHER PUBLICATIONS

Jochen Wilhelm et al., "SoFAR: Software for Fully Automatic Evaluation of Real-Time PCR data", Bio Techniques, vol. 34, No. 2, Feb. 28, 2003, pp. 324-333.
(Continued)

*Primary Examiner* — Alexander Satanovsky
*Assistant Examiner* — Lynda Dinh
(74) *Attorney, Agent, or Firm* — Dinsmore & Shohl, LLP

(57) ABSTRACT

Method of processing real-time PCR data, comprising: c) receiving a plurality of fluorescence melting curve data of real time PCR-experiments performed by a real-time PCR device with at least two fluorescence channels, and configured to perform the following steps multiple times, while increasing a temperature: i) at first moments in time measuring a first temperature value and a first radiation value corresponding to a first fluorescence channel; ii) at second moments in time measuring a second temperature value and a second radiation value corresponding to a second fluorescence channel; d) storing the plurality of temperature values and radiation values; e) determining a plurality of time-shifted second radiation values by linearly interpolating between two measured second radiation values, using weighting factors defined by the measured temperature values; f) after performing step e), calculating color corrected first radiation values, and color corrected second radiation values.

17 Claims, 23 Drawing Sheets

(51) Int. Cl.
*C12Q 1/68* (2018.01)
*C12Q 1/686* (2018.01)

(52) U.S. Cl.
CPC . *G01N 21/6428* (2013.01); *G01N 2021/6421* (2013.01); *G01N 2021/6439* (2013.01); *G01N 2201/121* (2013.01); *G01N 2201/129* (2013.01)

(58) Field of Classification Search
CPC ..... G01N 2021/6439; G01N 2201/121; G01N 2201/129
See application file for complete search history.

(56) References Cited

U.S. PATENT DOCUMENTS

| | | | | |
|---|---|---|---|---|
| 6,472,156 | B1* | 10/2002 | Wittwer | C12Q 1/6818 435/6.1 |
| 6,598,013 | B1 | 7/2003 | Domnisoru et al. | |
| 7,839,507 | B2 | 11/2010 | Gunstream et al. | |
| 8,137,616 | B2* | 3/2012 | Sagner | C12Q 1/6851 422/50 |
| 2011/0039274 | A1 | 2/2011 | Ludowise | |
| 2012/0101740 | A1 | 4/2012 | Orpana et al. | |
| 2012/0171677 | A1* | 7/2012 | Ludowise | G16B 25/00 435/6.11 |
| 2015/0247209 | A1* | 9/2015 | Sanford | C12Q 3/00 435/3 |
| 2017/0032083 | A1† | 2/2017 | Uten | |

FOREIGN PATENT DOCUMENTS

| | | | |
|---|---|---|---|
| EP | 1770172 | A2 † | 4/2007 |
| EP | 2107482 | A2 | 10/2009 |
| WO | WO9746714 | A1 | 12/1997 |
| WO | WO2007087336 | A2 | 8/2007 |
| WO | 2015155749 | A1 † | 10/2015 |

OTHER PUBLICATIONS

Würth, et al., "Comparison of Methods and Achievable Uncertainties for the Relative and Absolute Measurement of Photoluminescence Quantum Yields", Analytical Chemistry, 2011, vol. 83, pp. 3431-3439.
Stefan Rödiger et al., "Surtace Melting Curve Analysis with R", The R Journal, vol. 5/2, Dec. 2013; pp. 37-52.
Pabinger et al., "A survey of tools for the analysis of quantitative PCR (qPCR) data", Bimolecular Detection and Quantification, 2014, pp. 23-33.
Tobias P. Mann, "Automated Validation of Polymerase Chain reaction Amplicon Melting Curves", Journal of Bioinformatics and Computational Biology, vol. 4, No. 2, 2006; pp. 299-315.
Christopher Snow, "Flow Cytometer Electronics", Cytometry Part A, vol. 57A; pp. 63-69, 2004.
Wittwer, et al., "RealMultiplex PCR Assays", Methods, vol. 25, pp. 430-442, 2001.
Elenitoba-Johnson, et al., "Multiplex PCR by multicolor fluorimetry and fluorescence melting curve analysis", Nature Medicine, vol. 7, No. 2, Feb. 2001, pp. 249-253.
Bagwell, et al., "Fluorescence Spectral Overlap compensation for Any Number of Flow Cytometry Parameters", Annals New York Academy of Sciences, 1993, pp. 167-184.
Hermann, et al., "Amplicon DNA Melting Analysis for Mutation Scanning and Genotyping: Cross-Platform Comparison of Instruments and Dyes", Clinical Chemistry, vol. 52, No. 3, pp. 494-503, 2006.
Hatch, et al., "Continuous flow real-time PCR device using multi-channel fluorescence excitation and detection", Royal Society of Chemistry, 2014, pp. 1-7.
European Patent Office Third Party Submissions dated Nov. 22, 2019 in co-pending European Patent Application No. 15727454.9.
Office Action dated Feb. 25, 2020 in co-pending Chinese Patent Application No. CN201580025905.7.
International Search Report and Written Opinion dated Jul. 29, 2015 for PCT/IB2015/0521667 filed Apr. 13, 2015, pp. 1-11.
"Comparison of nine different real-time PCR chemistries for qualitative and quantitative applications in GMO election", Meti Buh Gasparic, et al., Analytical and Bioanalytical Chemistry, Springer, Berlin, DE, Mar. 1, 2010 vol. 396, No. 6.
Sigmoidal curve-fitting redefines quatitative real-time PCR with the prospective of developing automated high-throughput applications, RG—Rutledge, Nucleic Acids Research, Dec. 14, 2004, vol. 32, No. 22.
"Monitoring temperature with fluorescence during real-time PCR and melting analysis", Lindsay N. Sanford, Carl T. itter, Analytical Biochemistry, Mar. 2013.
Belgium Search Report completed Dec. 3, 2014 for BE 201400251 Filed Apr. 11, 2014. pp. 1-10.

\* cited by examiner
† cited by third party

| | TS-CC-BS-MA | BS-TS-CC-MA | TS-BS-CC-MA | CC-TS-BS-MA | CC-BS-TS-MA | BS-CC-TS-MA |
|---|---|---|---|---|---|---|
| Correct callings | 805 | 794 | 794 | 757 | 757 | 751 |
| sensitivity | 98.65% | 97.54% | 97.54% | 92.77% | 92.77% | 92.26% |
| balanced accuracy | 96.76% | 96.42% | 96.37% | 95.31% | 95.31% | 95.14% |

```
▼<Acq Number="15">
  ▼<Chan Number="0">
      <prop name="Fluor">2.57419939118193</prop>
      <prop name="Temp">54.21</prop>
      <prop name="Time">367720</prop>
    </Chan>
  ▼<Chan Number="1">
      <prop name="Fluor">2.0929223462781</prop>
      <prop name="Temp">53.88</prop>
      <prop name="Time">365690</prop>
    </Chan>
  ▼<Chan Number="2">
      <prop name="Fluor">6.43397901736032</prop>
      <prop name="Temp">54.55</prop>
      <prop name="Time">369760</prop>
    </Chan>
  </Acq>
▼<Acq Number="16">
  ▼<Chan Number="0">
      <prop name="Fluor">2.54827214929294</prop>
      <prop name="Temp">55.18</prop>
      <prop name="Time">373840</prop>
    </Chan>
  ▼<Chan Number="1">
      <prop name="Fluor">2.0636199830274</prop>
      <prop name="Temp">54.88</prop>
      <prop name="Time">371800</prop>
    </Chan>
  ▼<Chan Number="2">
      <prop name="Fluor">6.35577755135949</prop>
      <prop name="Temp">55.54</prop>
      <prop name="Time">375870</prop>
    </Chan>
  </Acq>
▼<Acq Number="17">
  ▼<Chan Number="0">
      <prop name="Fluor">2.51860293771736</prop>
      <prop name="Temp">56.19</prop>
      <prop name="Time">379980</prop>
    </Chan>
```

FIG 23

METHODS FOR FLUORESCENCE DATA CORRECTION

CROSS-REFERENCE TO RELATED APPLICATIONS

This application claims the benefit as a continuation-in-part of U.S. Provisional application Ser. No. 15/303,105, filed Oct. 10, 2016, entitled METHODS FOR FLUORESCENCE DATA CORRECTION, which is a national stage entry of PCT/IB2015/052667, filed Apr. 13, 2015, entitled METHODS FOR FLUORESCENCE DATA CORRECTION, which claims priority to Belgium App. No. BE2014/0251 filed Apr. 11, 2014, the entireties of which are incorporated by reference herein.

TECHNICAL FIELD

The present disclosure relates to computer implemented methods for data correction, and more in particular to methods of processing real-time polymerase chain reaction (PCR) data related to a sample to be analyzed.

BACKGROUND

Although the concept of using (computer implemented) methods for analyzing real-time PCR data is known in the art, known methods are mostly integrated in the measurement systems themselves, and have some drawbacks in terms of accuracy and/or flexibility.

BRIEF SUMMARY

It is an aim of the present disclosure to provide a (computer implemented) method of capturing and processing real-time PCR data related to a sample to be analyzed.

It is also an aim of the present disclosure to provide a real-time PCR device with an improved internal processing.

It is also an aim of the present disclosure to provide a computer implemented method of processing real-time PCR data related to a sample to be analyzed which is captured by a real-time PCR device, and which can be executed outside of the PCR device, for example on a computer.

It is also an aim of the present disclosure to provide a computer program product for performing such a method.

It is a particular aim of the present disclosure to provide such methods which provide more accurate data than existing methods.

It is an aim of particular embodiments of the present disclosure to provide a method in which cross-talk between multiple fluorescence channels is more accurately treated.

These and other objectives are accomplished by a computer implemented method, and a real-time PCR device, and by a computer program product according to embodiments of the present disclosure.

According to a first aspect, the present disclosure provides a method of capturing and processing real-time PCR data related to a sample to be analyzed, the method comprising the steps of: a) providing a real-time PCR device capable of capturing multispectral fluorescence data indicative of at least two fluorescence channels having partially overlapping frequency spectra; c) measuring a plurality of fluorescence melting curve data of real time PCR-experiments of said sample using said PCR device, by performing the following steps multiple times, while increasing a temperature inside said realtime PCR device: i) at a first moment in time measuring a first temperature value and measuring a first radiation value corresponding to a first of said at least two fluorescence channels; ii) at a second moment in time different from the first moment in time, measuring a second temperature value and a second radiation value corresponding to a second of said at least two fluorescence channels, different from the first fluorescence channel; d) storing the plurality of measured first and second temperature values and first and second radiation values; e) determining a plurality of time-shifted second radiation values by linearly interpolating between two measured second radiation values, using weighting factors defined by the corresponding measured temperature values; f) after performing step e), calculating color corrected first radiation values, and determining color corrected second radiation values using predefined coefficients.

The predefined coefficients may be determined by a calibration test, performed on said realtime PCR device, or in any other way.

Step d) may comprise storing said values in a volatile memory (e.g. RAM) and/or in a non-volatile memory (e.g. a hard disk, a network drive, a flash drive, a memory stick, etc), or in the cloud, or in any other way.

It is a major advantage of this embodiment that the "time-shift" correction is performed based on actual measured temperature values (for each well), and not simply using a "constant time period" for all the wells. Tests have shown that this approach yields more accurate results, and while the inventors do not wish to be bound by any theory, this is probably because local temperature differences between the particular wells (e.g. due to the particular location on the tray) are taken into account, moreover in a relatively simple and automatic way, without having to use a highly complex mathematical model of the thermal behavior of a particular array within the device.

It is pointed out that for a majority of the cases (e.g. more than 90% of the cases) the at first sight tiny differences between the method described in the present disclosure and the prior art methods, ultimately end in the same clinical interpretation, but the true benefit of the method according to the present disclosure lies in the small number of cases (e.g. smaller than 10% of the cases) where the clinical interpretation is not the same. While mathematically this may seem like a small number, in practice it means that a person is diagnosed to have a certain disease or not, which may have huge consequences for that person. Therefore, even a 1% difference in accuracy can mean that a particular person's life is either saved (if a particular disease is correctly diagnosed) or destroyed (if the diagnosis based on this data is incorrect).

This method can be used for example for gene detection, for gene expression analysis, genetic variation analysis, etc.

It is an advantage of time-shifting some of the radiation values, rather than using the measured data as such in the color conversion step, because by doing the time-shift, the radiation values of the different channels are radiation values that would be obtained if the measurements of the different channels were taken at exactly the same temperatures in each of the wells.

The color correction step typically involves matrix operations, but any other suitable color correction may also be used.

In case there are more than two fluorescence channels, step c) would include further measurements, and step e) would include further time-shifts, and step f) would include further color compensation.

In an embodiment, step e) comprises determining the time-shifted second radiation values according to the following formulas or equivalent formulas:

$$\begin{cases} R630 \mathrel{*}= m*(T650-T630), \text{ and} \\ m = (R660-R630)/(T660-T630) \end{cases},$$

where T650 is a temperature measurement of the first channel, R630 and T630 are a radiation value and an associated temperature value of a measurement of the second channel taken before the measurement of the first channel, and R660 and T660 are a radiation value and an associated temperature value of a measurement of the second channel taken after the temperature measurement of the first channel These formulas reflect a linear interpolation between two consecutive second radiation values (in the example between the values R630 taken at time t700 and R660 taken at time t703), but contrary to what may be expected, the inventors have not simply determined the average in case of two fluorescence signals, or calculated a weighted average using the weight factors (⅓) and (⅔) in case of three fluorescence signals. Instead, the inventors use a weighted average where the weight factors are not constant, even if the time intervals between the measurements are perfectly periodic, but the weight factors are calculated based on the actually measured temperature values, as described.

As already stated above, it is a major advantage that this "time-shift" correction is performed based on the actually measured temperature values associated with each well.

In an embodiment, the real-time PCR device is capable of capturing multispectral fluorescence data indicative of at least three fluorescence channels having a partial spectral overlap, and wherein step c) further comprises: iii) at a third moment in time different from the first and second moment in time, measuring a third temperature value and a third radiation value corresponding to a third of said at least three fluorescence channels, different from the first and second fluorescence channel; and wherein step e) further comprises: determining time-shifted third radiation values by linearly interpolating between two measured third radiation values, using weighting factors defined by the corresponding measured temperature values.

This is a variant of the method described above, but instead of at least two fluorescence channels, there are at least three fluorescence channels.

In an embodiment, step e) comprises determining the time-shifted third radiation value of the third channel according to the following formulas or equivalent formulas:

$$\begin{cases} R640 \mathrel{*}= m*(T650-T640), \text{ where} \\ m = (R665-R640)/(T665-T640) \end{cases},$$

where T650 is a temperature measurement of the first channel, R640 and T640 are a radiation value and a temperature value of a measurement of the third channel taken before the measurement of the first channel, and R665 and T665 are a radiation value and a temperature value of a measurement of the third channel taken after the temperature measurement of the first channel.

In an embodiment, the method further comprises the step of: b) disabling a color compensation function of said real-time PCR device, if present, said color compensation function adapted for reducing cross-talk between said at least two fluorescence channels.

It is an advantage of this embodiment, that more correct values can be obtained by starting from the raw measured data, and performing the color compensation on the time-shifted values, in the manner as described above (where the interpolation is done by taking into account the measured temperature values).

In an embodiment, the method further comprises step g) following step f) of: g) determining a first background signal for the first color corrected values, and subtracting the determined first background signal from the first color corrected values to obtain first baseline corrected values, and determining a second background signal for the second color corrected values, and subtracting the determined second background signal from the second color corrected values to obtain second baseline corrected values.

In this embodiment, a so called "baseline correction" is performed after the step of color correction (CC). As can be appreciated from FIG. 22, this order of the steps provides optimal results.

The baseline-corrected values may optionally be smoothed, e.g. using an averaging function with a sliding window.

In an embodiment, the method further comprises the step of smoothing or low pass filtering, the baseline corrected values.

The smoothing may be performed using a moving average function, using a "sliding window", in manners known per se in the art.

It is an advantage that in this way certain errors (such as e.g. quantization errors) can be reduced. In this way the risk of providing data having an arguable "shoulder" can be reduced, which ultimately also reduces the risk of false interpretation of this arguable shoulder position.

In an embodiment, the method further comprises the step of calculating a derivative of the baseline-corrected values versus temperature, thereby obtaining derivative data for each of the fluorescence channels, and further comprising the step of finding one or more local peaks or local shoulders in the derivative data.

In an embodiment, the method further comprises the step of presenting this derivative data on a graphics display device.

It is an advantage of showing this data on a physical display, because it allows a human to visually inspect the measured data. Most human beings are not capable of analyzing numerical information represented in tables, but they are very well capable of analyzing graphical data. In this way, the results provided by the method can be inspected by a physical person, typically a medically trained person.

In an embodiment, the method further comprises the step of: determining a presence or absence of one or more target molecules based on the derivative data.

This step may include correlating a subset of the derivative data, and/or peaks and/or shoulders thereof with known data, and interpreting the correlation results into diagnostic results, using a mathematical model and/or a decision tree.

The decision tree is typically constructed in such a way as to correlate certain diseases to the presence and position of peaks. Typically a correlation of peaks from multiple fluorescence channels (for example 3 or 4 or 5, or more than 5) are combined in order to come to a clinical result.

According to a second aspect, the present disclosure also provides a real-time PCR device configured for performing the methods according the first aspect.

According to a third aspect, the present disclosure also provides a computer implemented method of processing real-time PCR data related to a sample to be analyzed, the method comprising the steps of: c) receiving a plurality of fluorescence melting curve data of real time PCR-experiments of said sample performed by a real-time PCR device capable of capturing multispectral fluorescence data indicative of at least two fluorescence channels having partially overlapping frequency spectra, and which is configured to perform the following steps multiple times, while increasing a temperature inside said real-time PCR device: i) at a first moment in time measuring a first temperature value and measuring a first radiation value corresponding to a first of said at least two fluorescence channels; ii) at a second moment in time different from the first moment in time, measuring a second temperature value and a second radiation value corresponding to a second of said at least two fluorescence channels, different from the first fluorescence channel; d) storing the plurality of measured first and second temperature values and first and second radiation values; e) determining a plurality of time-shifted second radiation values by linearly interpolating between two measured second radiation values, using weighting factors defined by the corresponding measured temperature values; f) after performing step e), calculating color corrected first radiation values, and determining color corrected second radiation values using predefined coefficients.

In an embodiment, step e) comprises determining the time-shifted second radiation values using the following formulas or equivalent formulas:

$$\begin{cases} R630 \mathrel{*}= m*(T650-T630), \text{ where} \\ m = (R660-R630)/(T660-T630) \end{cases},$$

where T650 is a temperature measurement of the first channel, R630 and T630 are a radiation value and an associated temperature value of a measurement of the second channel taken before the measurement of the first channel, and R660 and T660 are a radiation value and an associated temperature value of a measurement of the second channel taken after the temperature measurement of the first channel.

In an embodiment, the real-time PCR device is capable of capturing multispectral fluorescence data indicative of at least three fluorescence channels having a partial spectral overlap, and wherein step c) further comprises: iii) at a third moment in time different from the first and second moment in time, measuring a third temperature value and a third radiation value corresponding to a third of said at least three fluorescence channels, different from the first and second fluorescence channel; and wherein step e) further comprises: determining time-shifted third radiation values by linearly interpolating between two measured third radiation values, using weighting factors defined by the corresponding measured temperature values.

In an embodiment, step e) comprises determining the time-shifted third radiation value of the third channel using the following formulas or equivalent formulas:

$$\begin{cases} R640 \mathrel{*}= m*(T650-T640), \text{ where} \\ m = (R665-R640)/(T665-T640) \end{cases},$$

where T650 is a temperature measurement of the first channel, R640 and T640 are a radiation value and a temperature value of a measurement of the third channel taken before the measurement of the first channel, and R665 and T665 are a radiation value and a temperature value of a measurement of the third channel taken after the temperature measurement of the first channel.

In an embodiment, the data received from the real-time PCR device was raw measurement data without color compensation for reducing cross-talk between said at least two fluorescence channels being performed by said real-time PCR device.

In an embodiment, the computer implemented method further comprises step g) following step f) of: g) determining a first background signal for the first color corrected values, and subtracting the determined first background signal from the first color corrected values to obtain first baseline corrected values, and determining a second background signal for the second color corrected values, and subtracting the determined second background signal from the second color corrected values to obtain second baseline corrected values.

In an embodiment, the computer implemented method further comprises the step of smoothing or low pass filtering, the baseline corrected values.

In an embodiment, the computer implemented method further comprises the step of calculating a derivative of the baseline-corrected values versus temperature, thereby obtaining derivative data for each of the fluorescence channels, and further comprises the step of finding one or more local peaks or local shoulders in the derivative data.

In an embodiment, the computer implemented method further comprises the step of presenting this derivative data on a graphical display device.

In an embodiment, the computer implemented method further comprises the step of: determining a presence or absence of one or more target molecules based on the derivative data.

According to a fourth aspect, the present disclosure also provides a computer program product containing executable instructions which perform the method according to the third aspect, when being executed on a computer device having or being connected to a display device.

BRIEF DESCRIPTION OF THE SEVERAL VIEWS OF THE DRAWINGS

The disclosure comprises various (computer implemented) sub-methods, for data correction, related systems, a real-time PCR device, software, and the use thereof, in particular suitable for fluorescence data, as well does the disclosure provides a preferred ordering of these sub-methods. The underlying software could be used as standalone or be integrated in the measuring equipment, and as such it may be functioning on a processor, it may be integrated in the measurement equipment, or various steps of the method may be split between several devices (e.g. partially on the measuring equipment, and partially on a standalone computer).

The underlying software could also consist of basic software and a part that is client- and/or application specific. The main inventive contribution concerns the recognition that the data obtained from the measuring equipment deviate from what could ideally be expected, even after processing the data with software integrated in the measurement equipment. Even more, said deviation could be caused by co-integrated software, and careful correction of the defects of the measuring equipment is thus necessary. This correction should preferably happen in various steps, even more so, preferably by sequencing these steps in a specific order.

A further inventive contribution is recognizing the fact that these corrections are client and/or application and/or measuring equipment specific, and as such providing sufficient options to deal herewith, for example by providing the possibility of using multiple data formats, calibration data and/or other settings parameters. However, the disclosure does not only focus on the correction of the data as such, but is also aimed at improving the use of data for detection of target molecules, more specific detection of infections, which is typically done via peak detection. The data analysis following the correction of the data must thus preferably be integrated in the software and also have the required parameters and validation methods.

The various aspects of the disclosure are described in the claims.

BRIEF DESCRIPTION OF THE DRAWINGS

Figure 1:
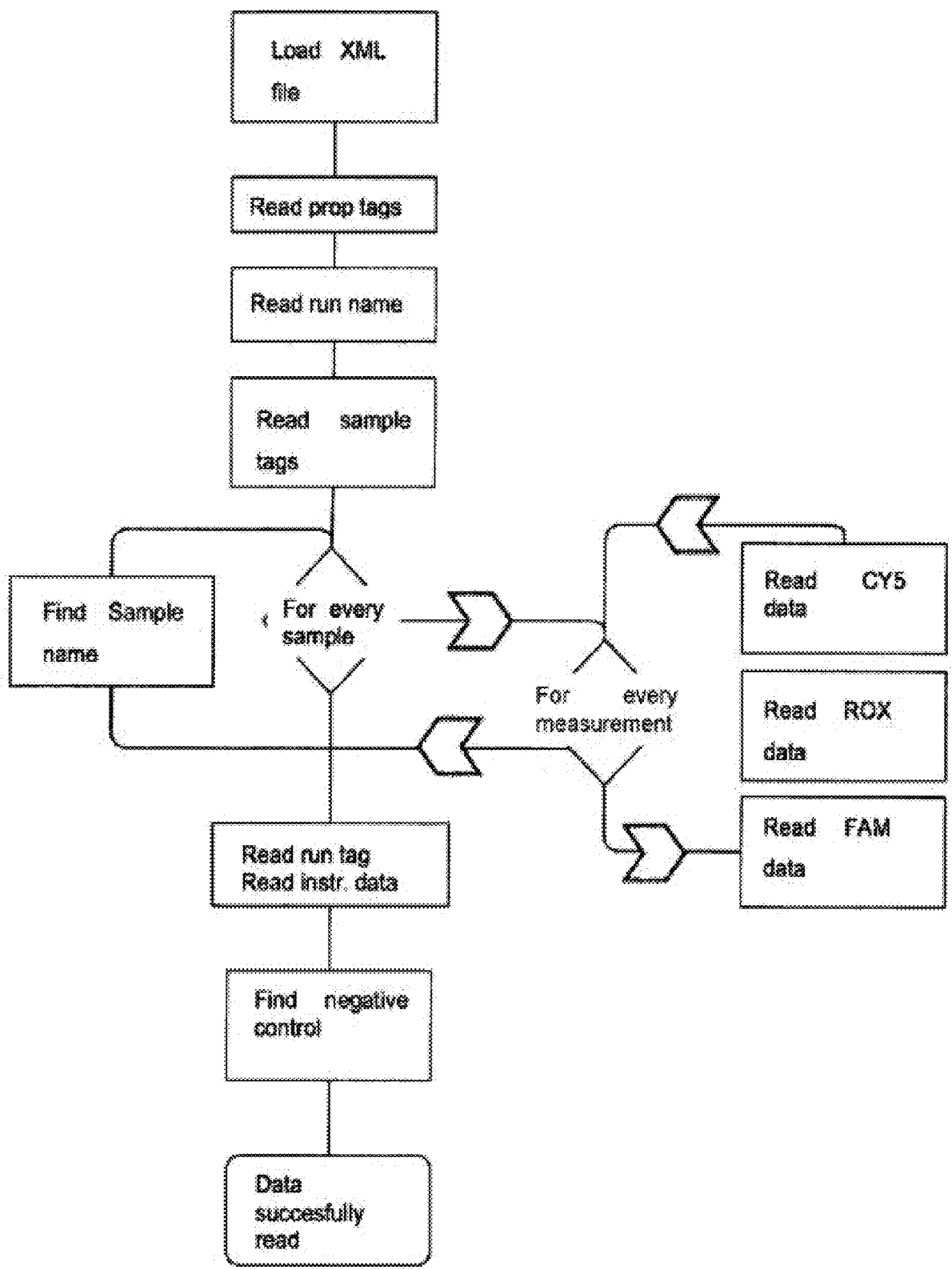

FIG. 1 shows a flow diagram of an embodiment of the present disclosure.

Figure 2:
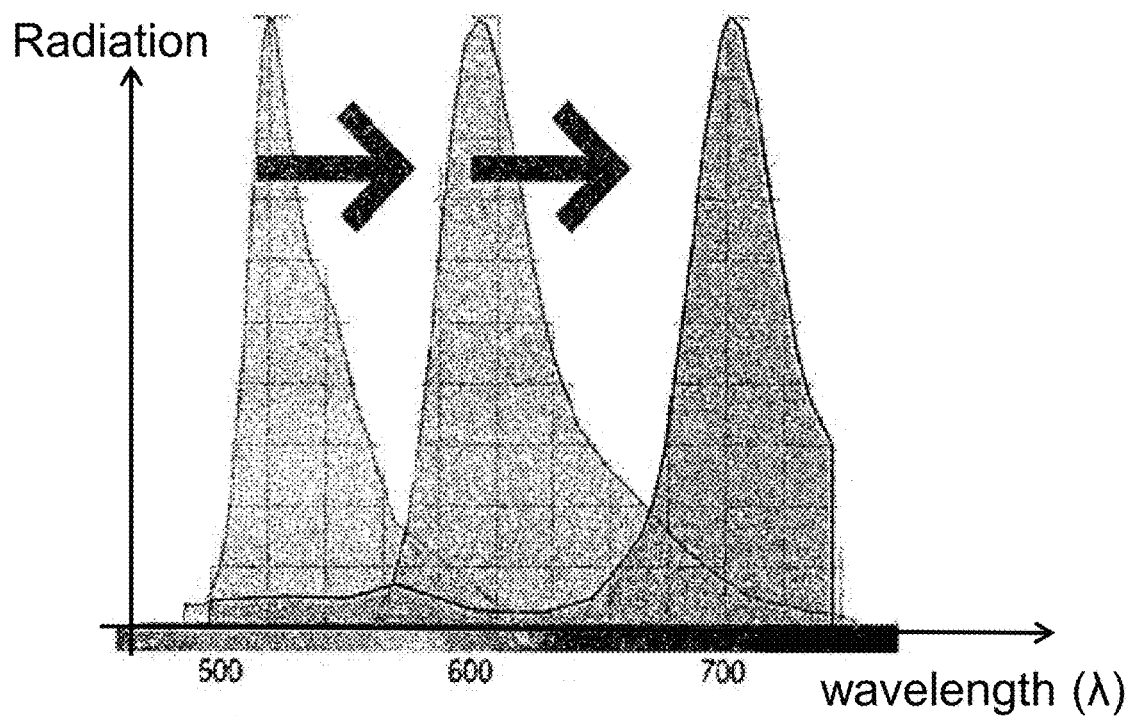

FIG. 2 shows a fluorescence frequency spectrum and the consequences of the time shift.

Figure 3:
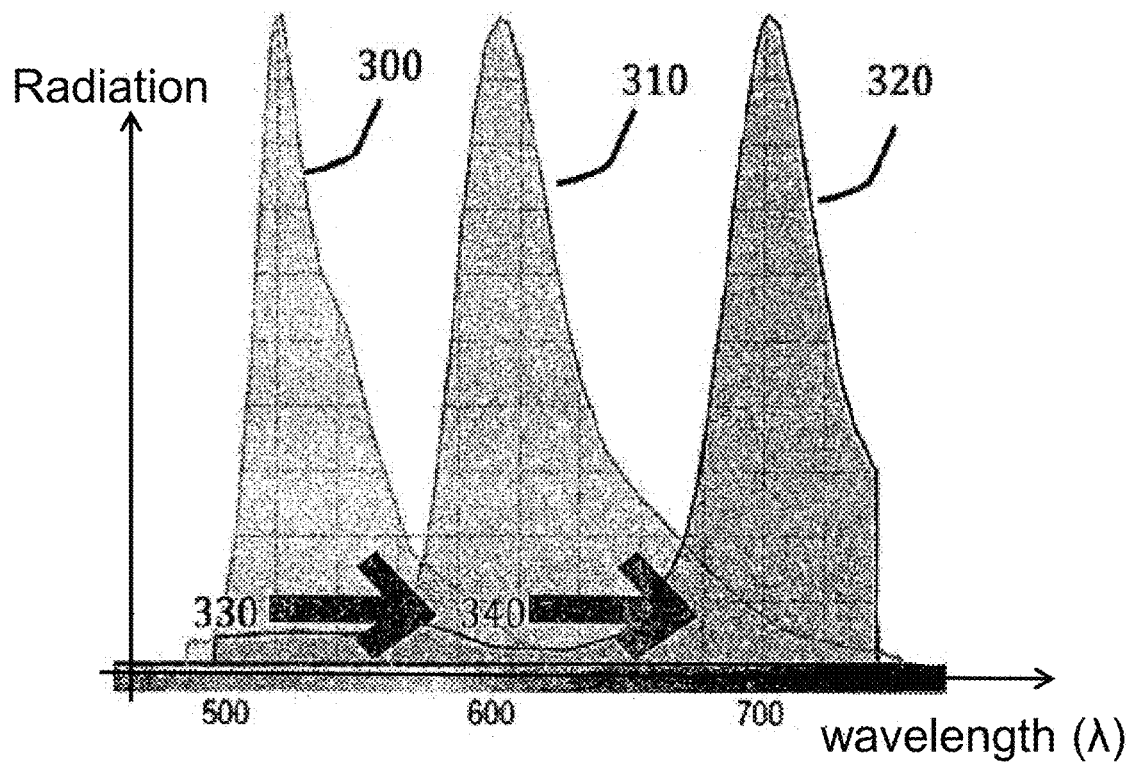

FIG. 3 shows the fluorescence frequency spectrum and the consequences of colour compensation.

Figure 4:
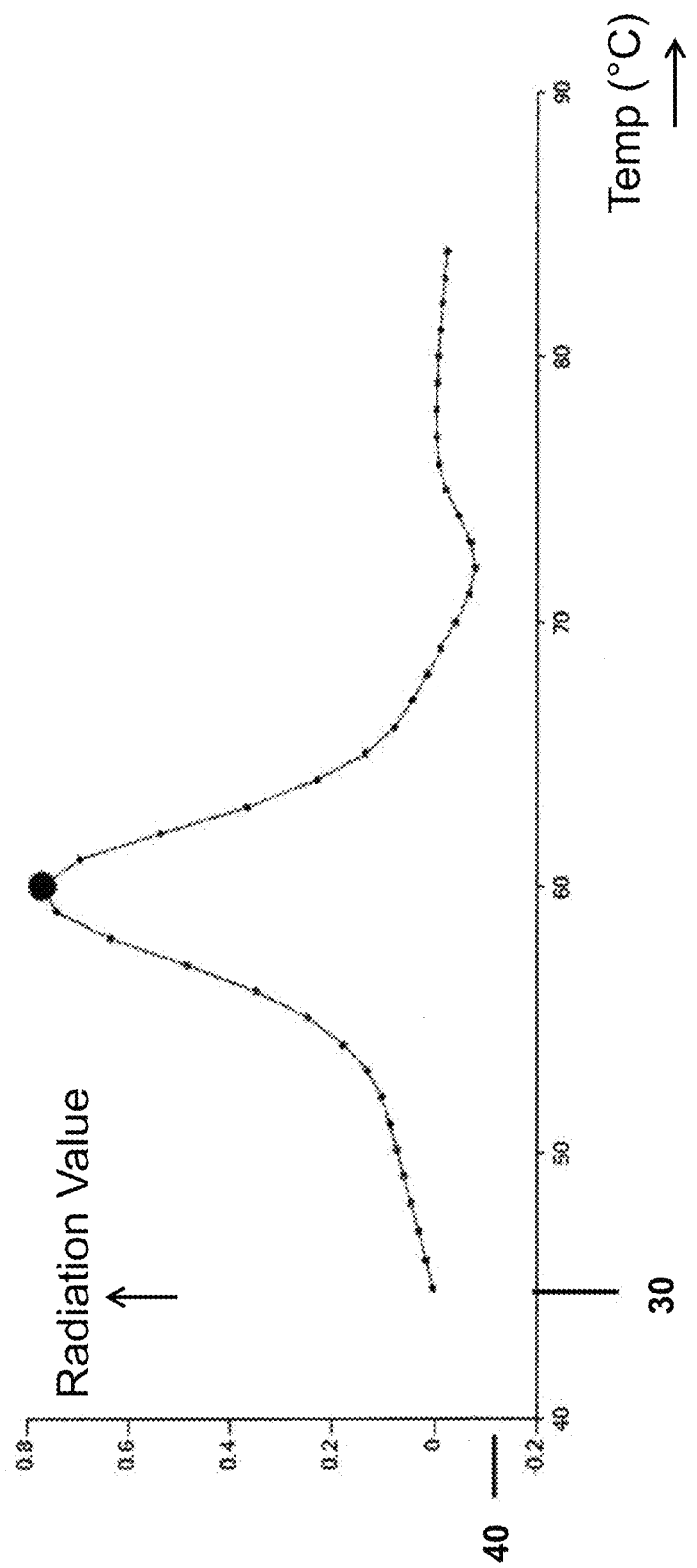

FIG. 4 shows a reference melting curve.

Figure 5:
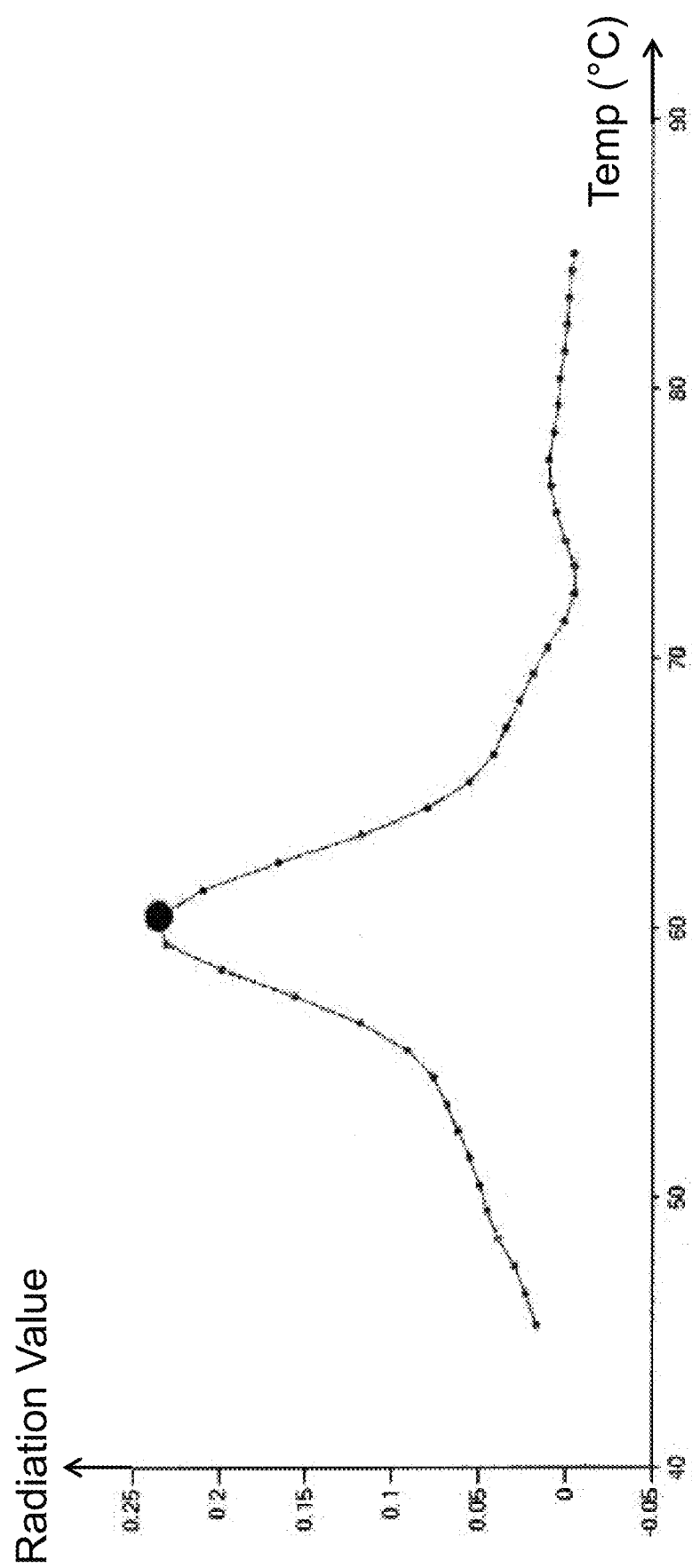

FIG. 5 shows a melting curve without compensation.

Figure 6:
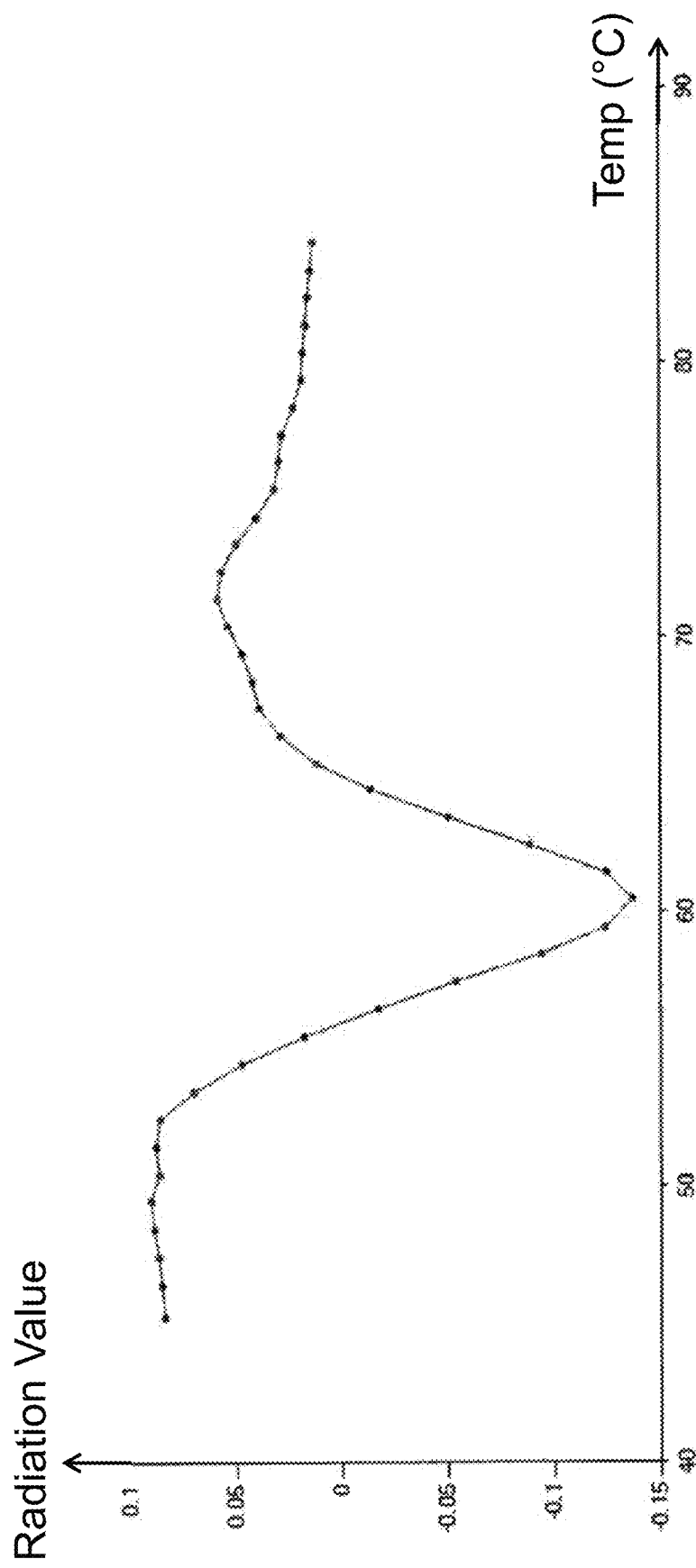

FIG. 6 shows a melting curve with compensation.

Figure 7:
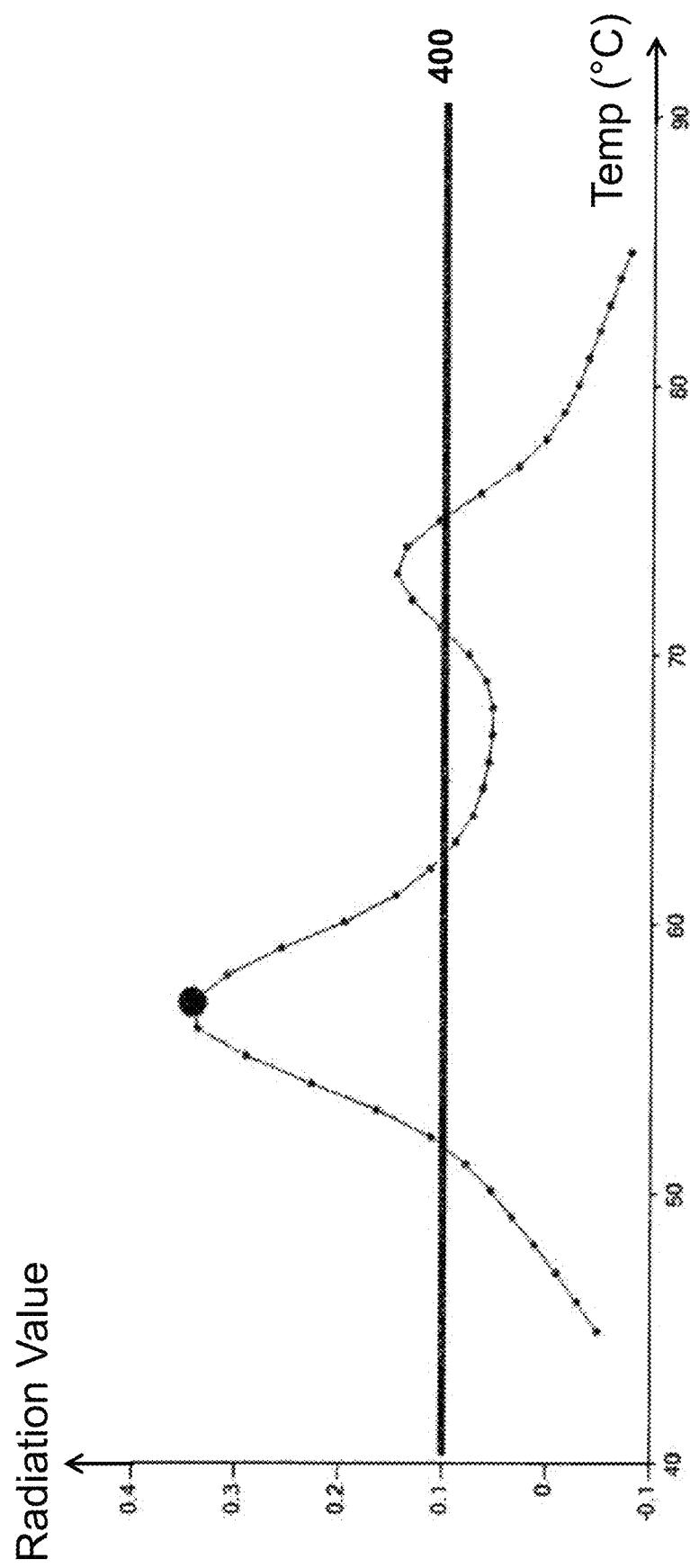

FIG. 7 shows data without subtraction of a background signal.

Figure 8:
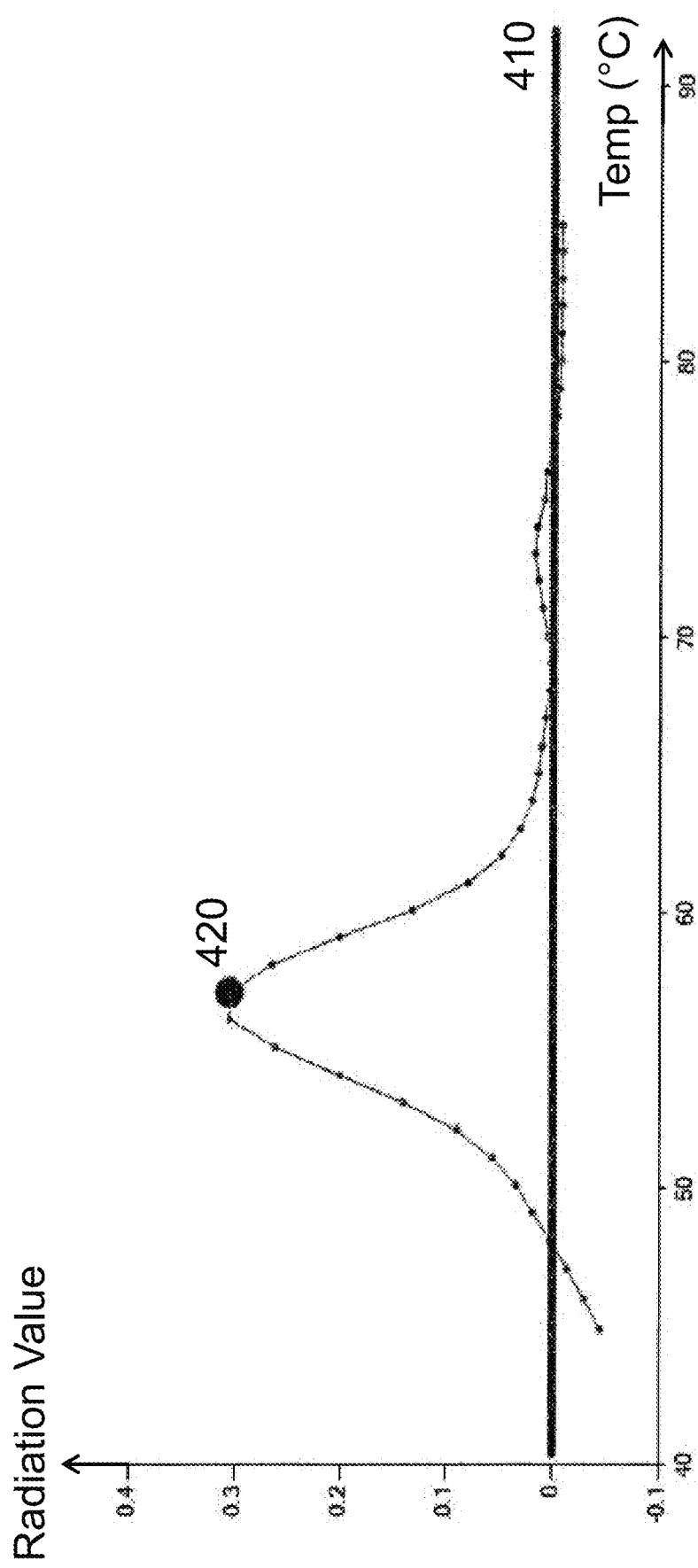

FIG. 8 shows data after subtraction of a background signal.

Figure 9A:
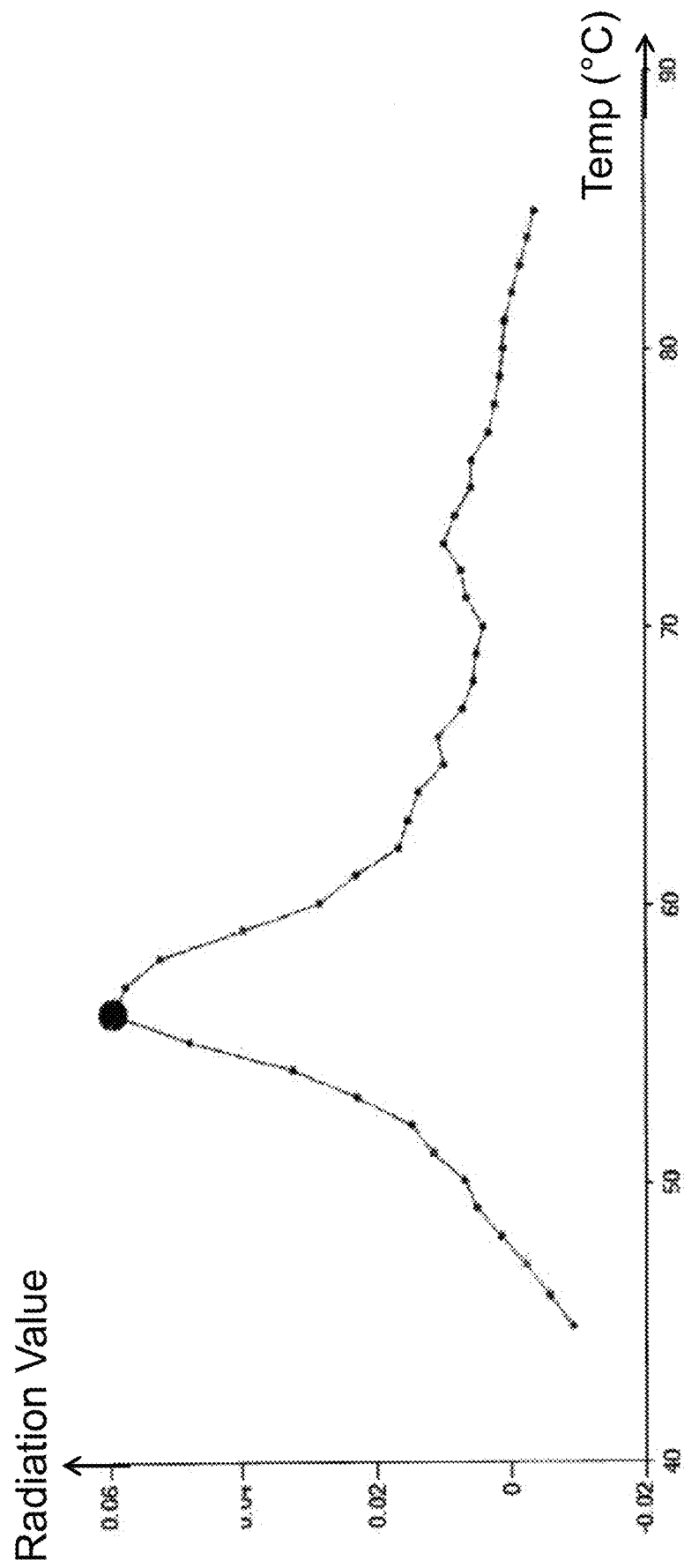

FIG. 9A shows a graph as described herein.

Figure 9B:
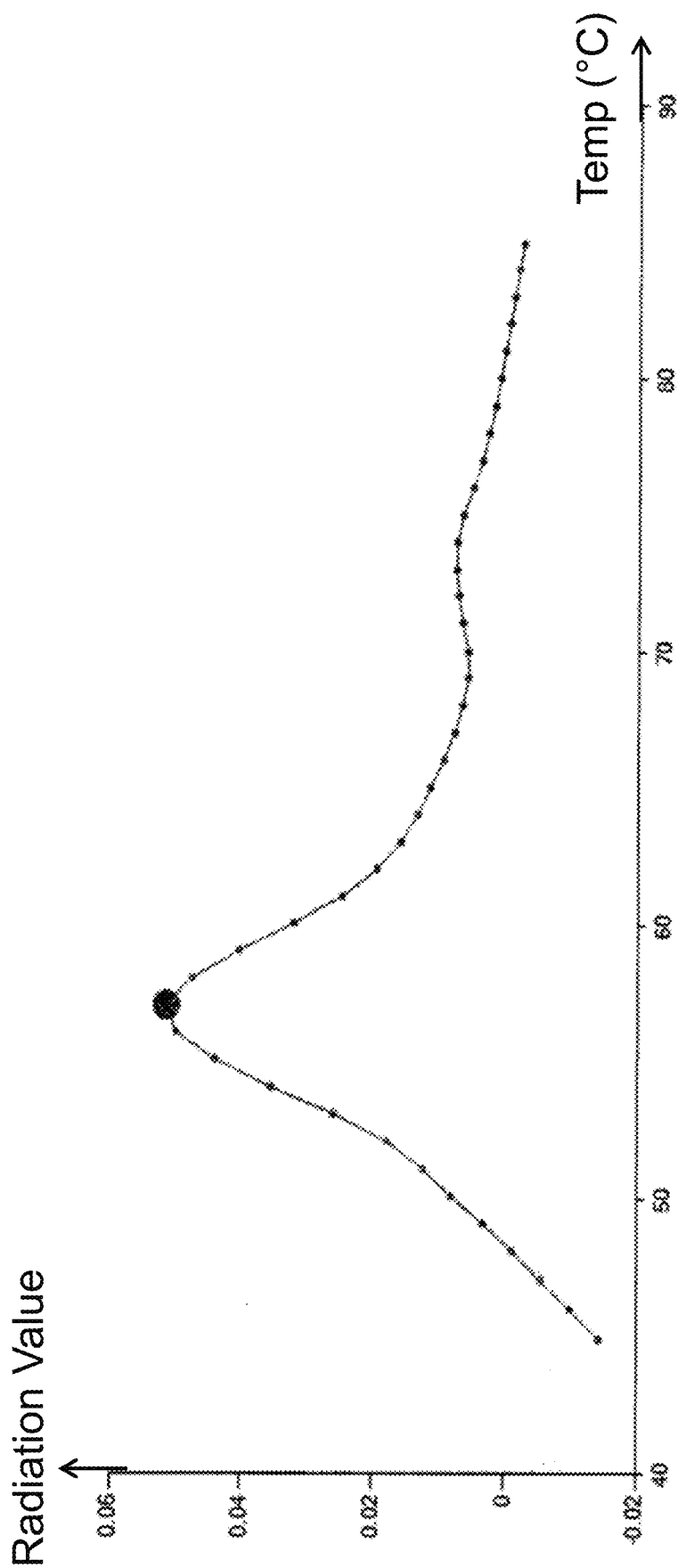

FIG. 9B shows the effect of using a moving average on the graph of 9A.

Figure 10:
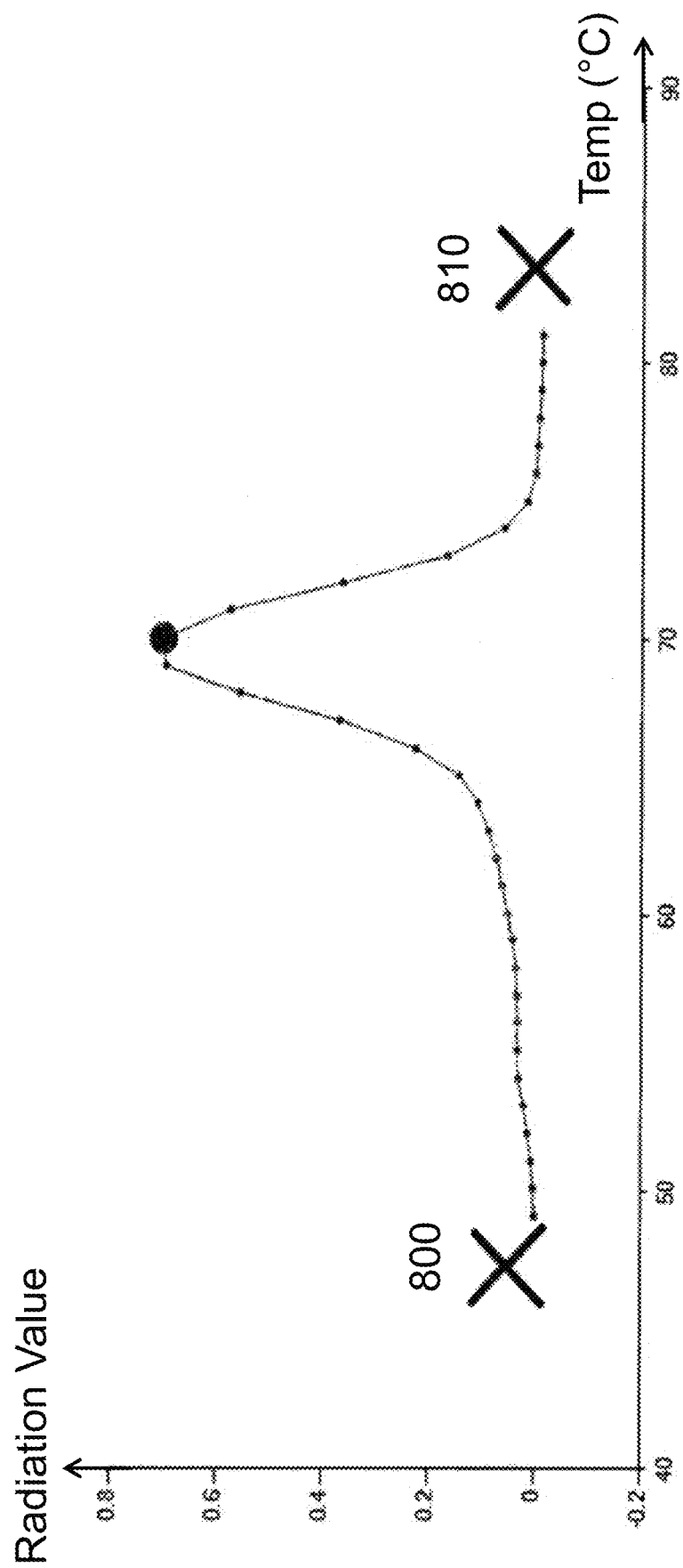

FIG. 10 illustrates the problems of loss of data points.

Figure 11:
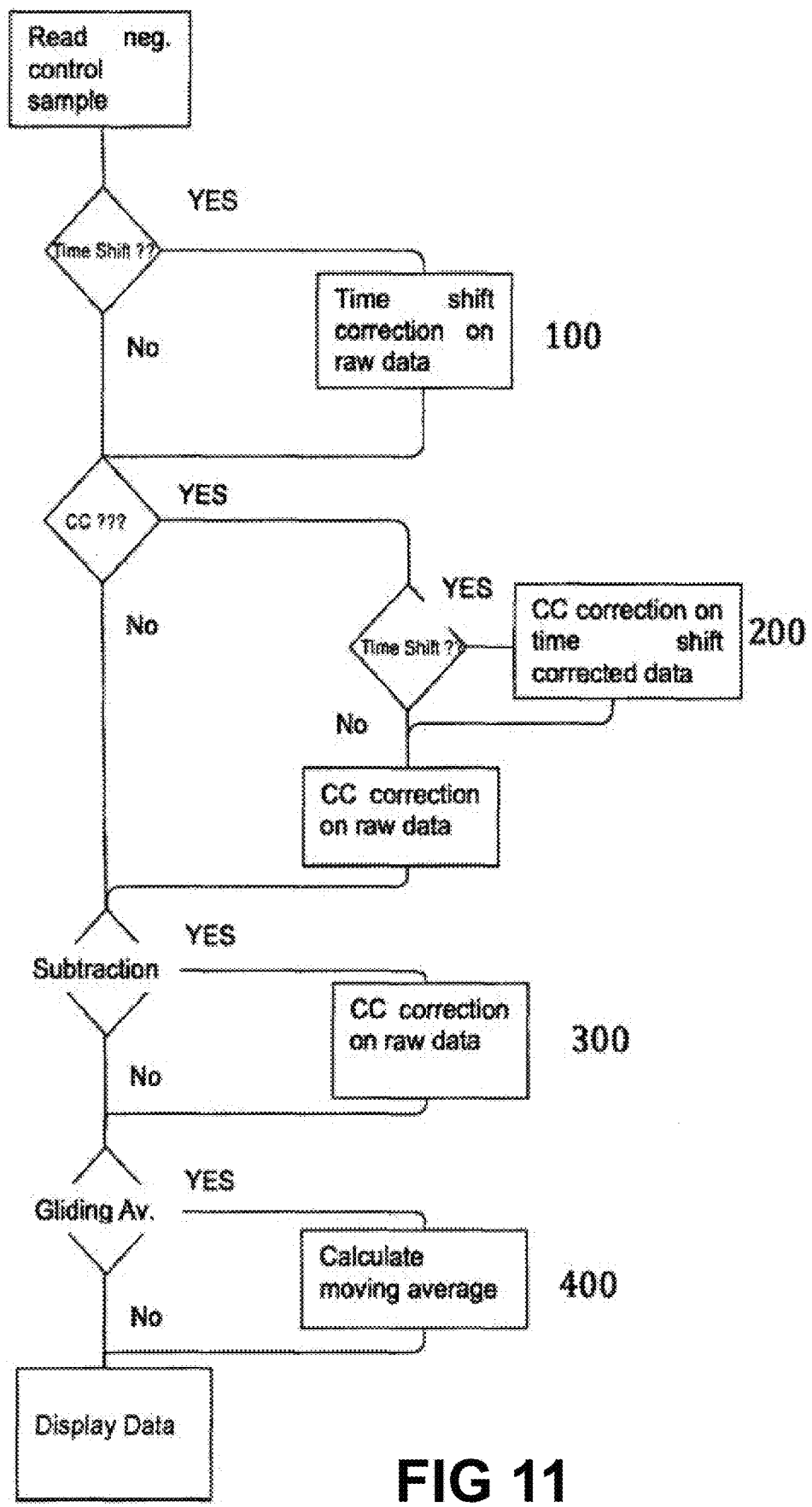

FIG. 11 shows a flow diagram of a method.

Figure 12:
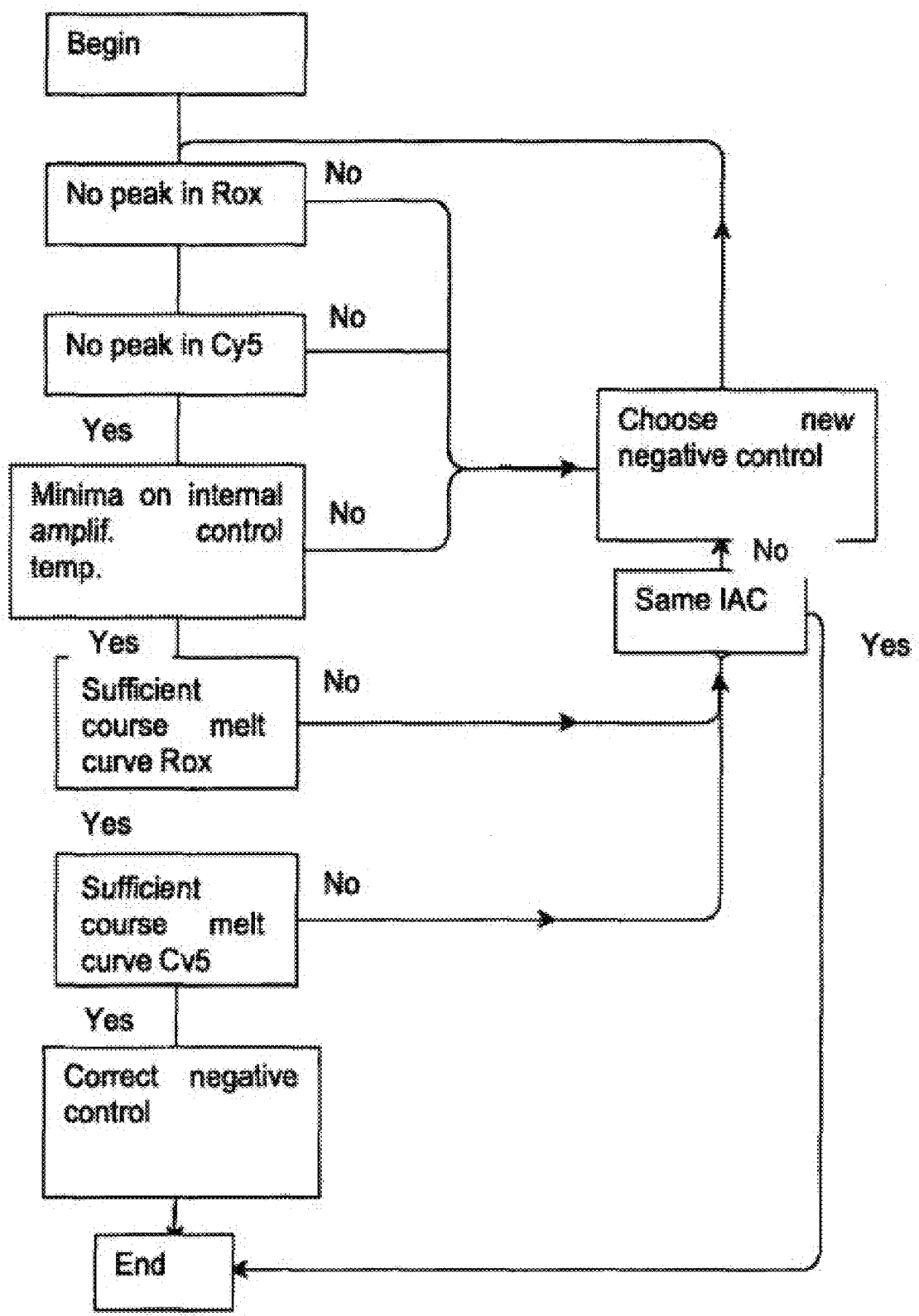

FIG. 12 shows the flow diagram of a validation method.

Figure 13:
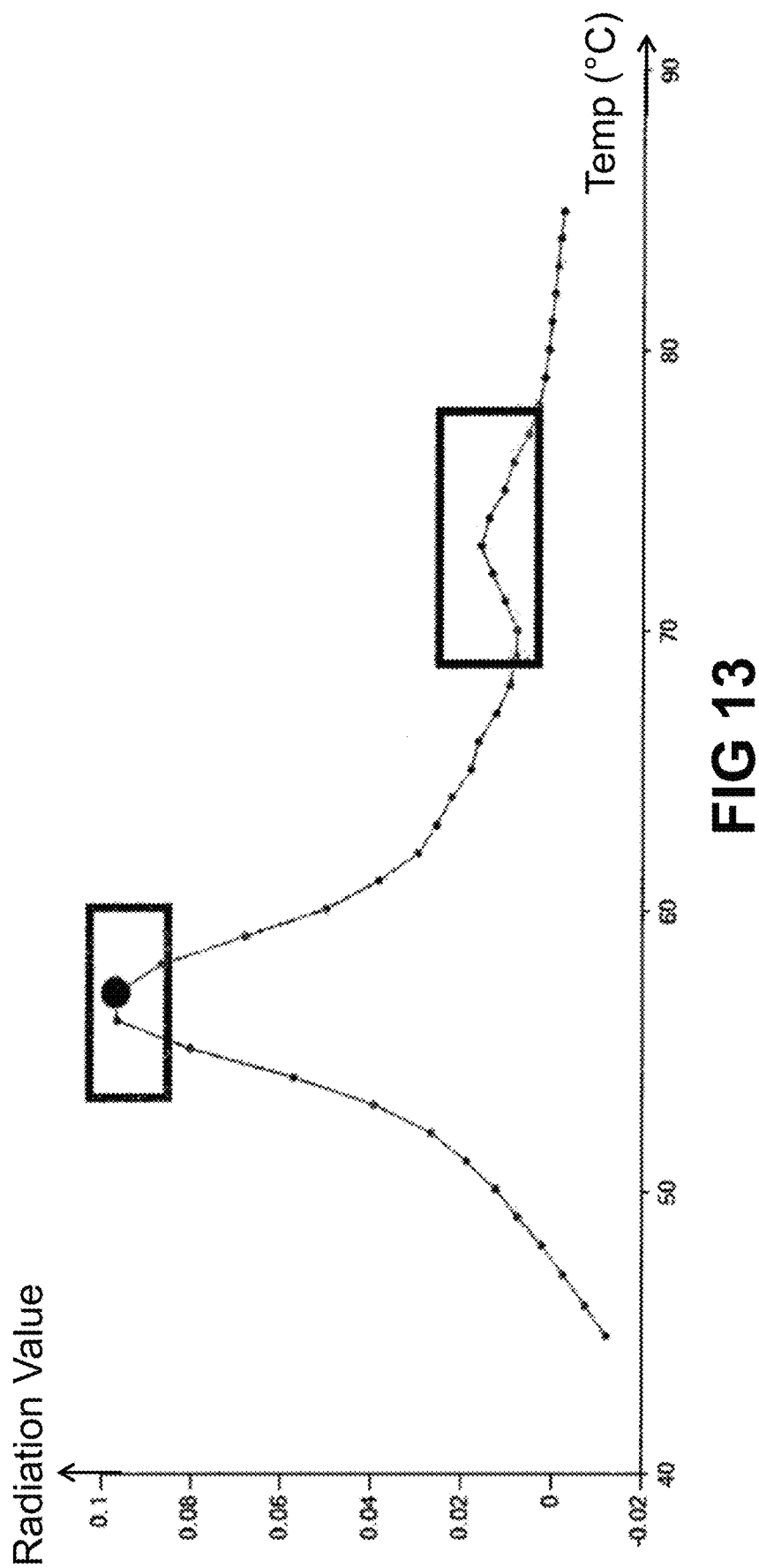

FIG. 13 illustrates a peak detection.

Figure 14:
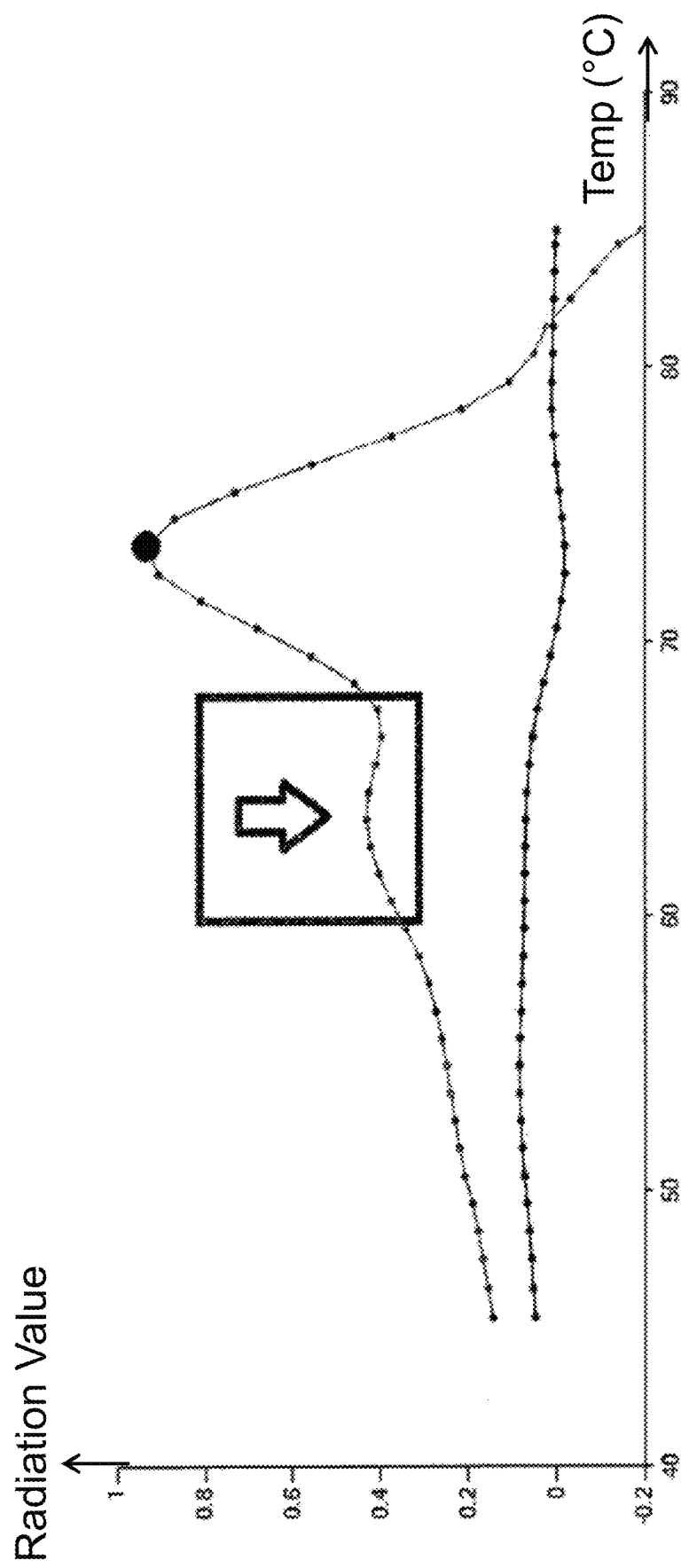

FIG. 14 illustrates a shoulder infection.

Figure 15:
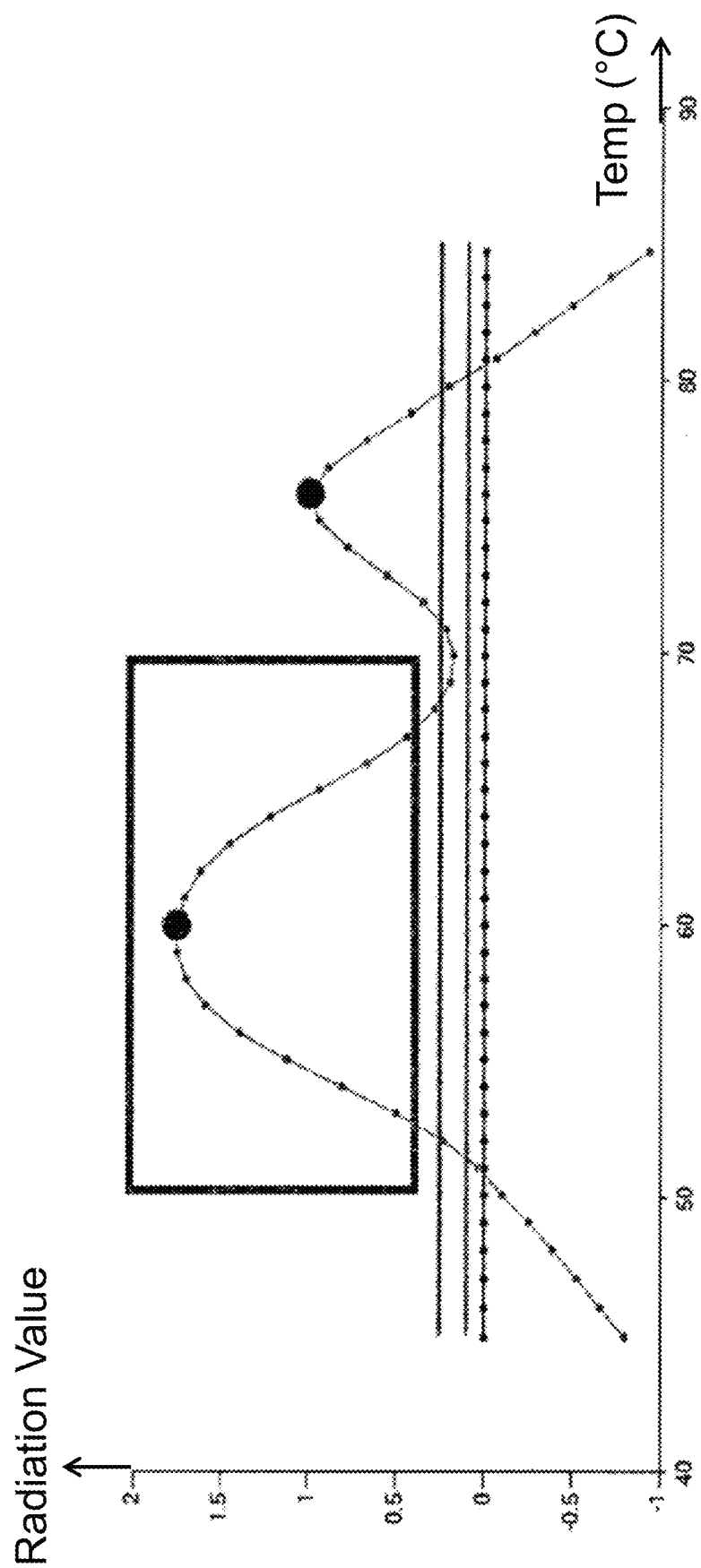

FIG. 15 illustrates a multiple infection.

Figure 16:
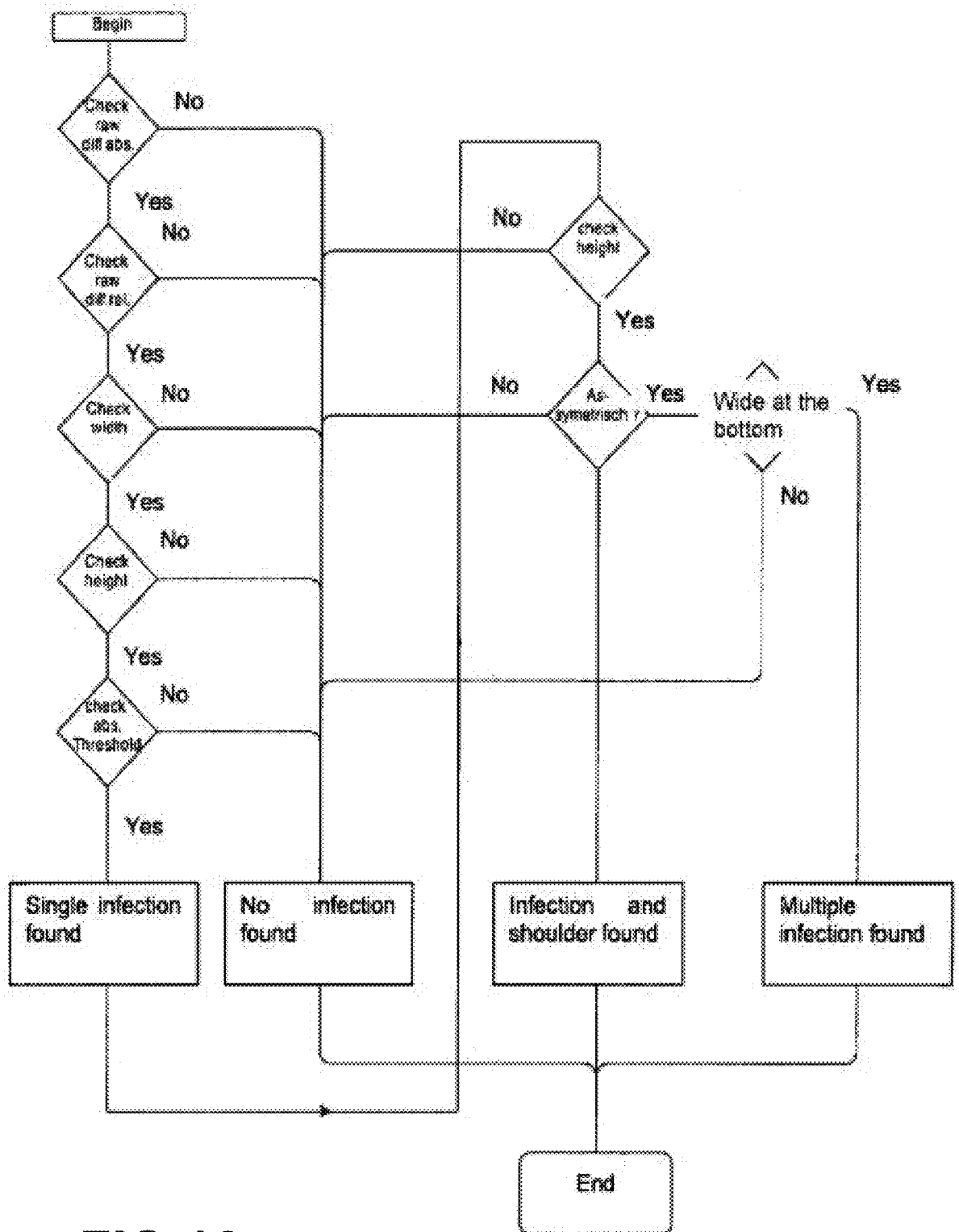

FIG. 16 illustrates a method for the data analysis.

Figure 17:
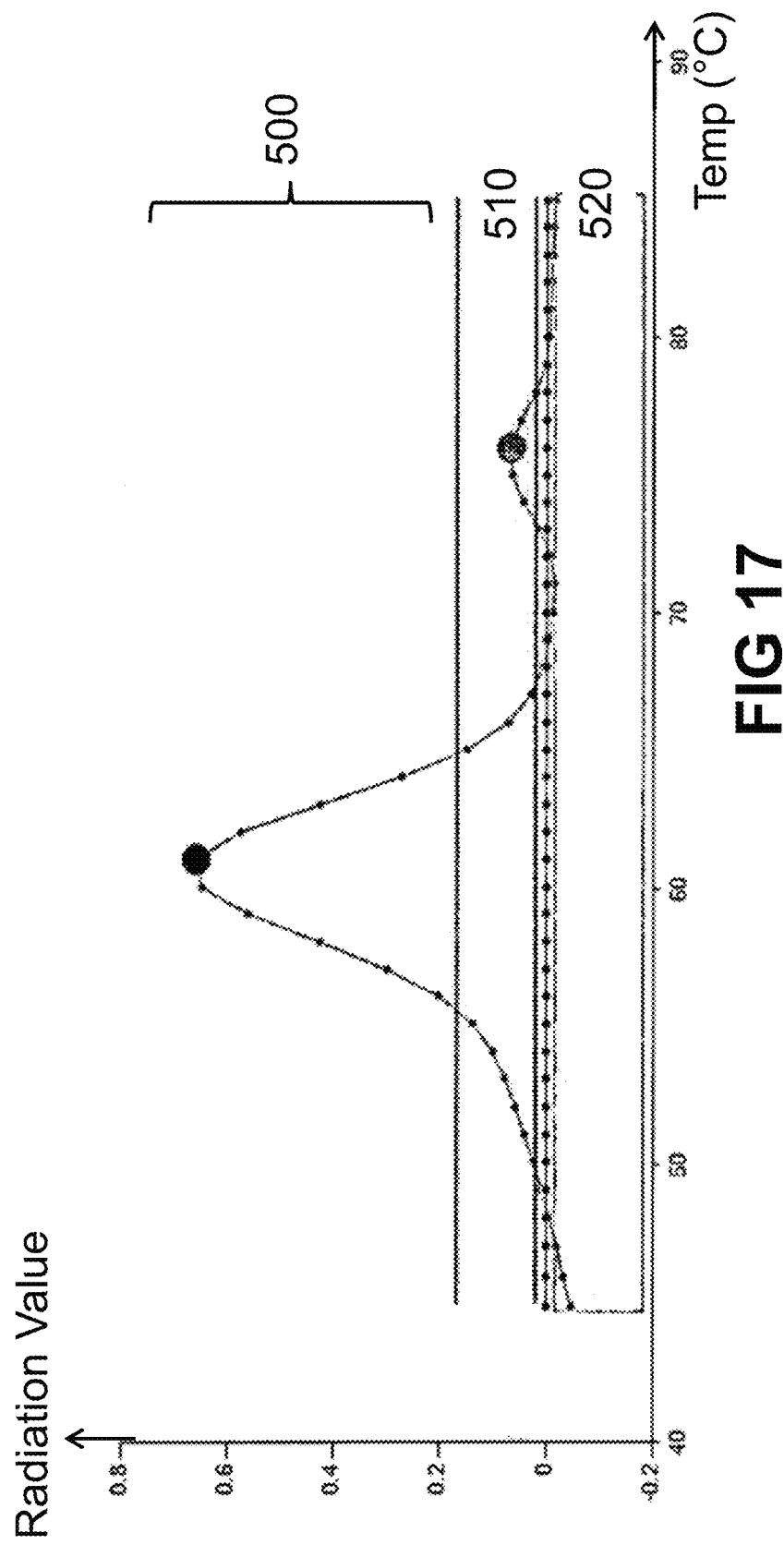

FIG. 17 illustrates the use of 3-value-score in various areas.

Figure 18:
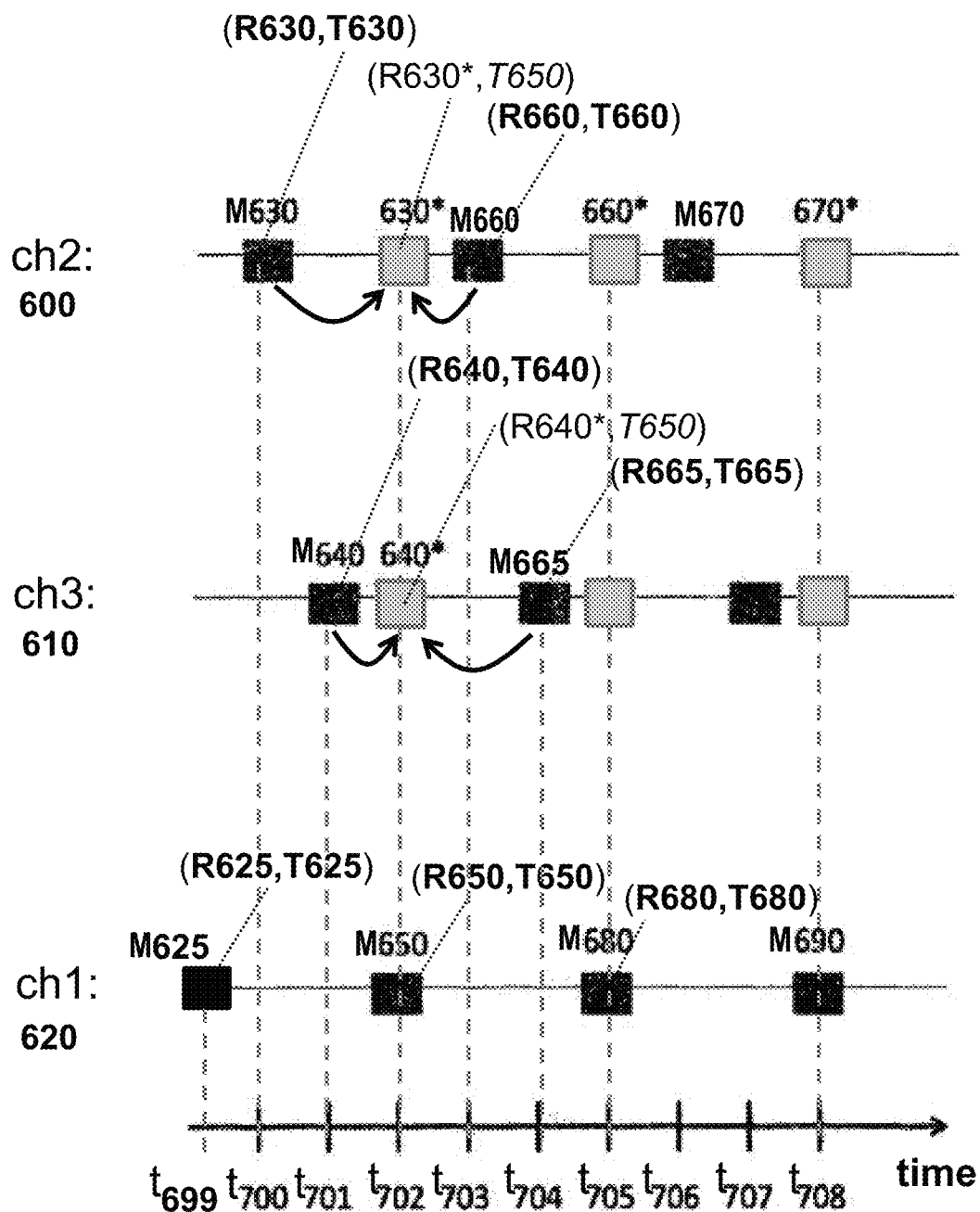

FIG. 18 illustrates the method of the "time shift" as proposed by the present disclosure.

Figure 19:
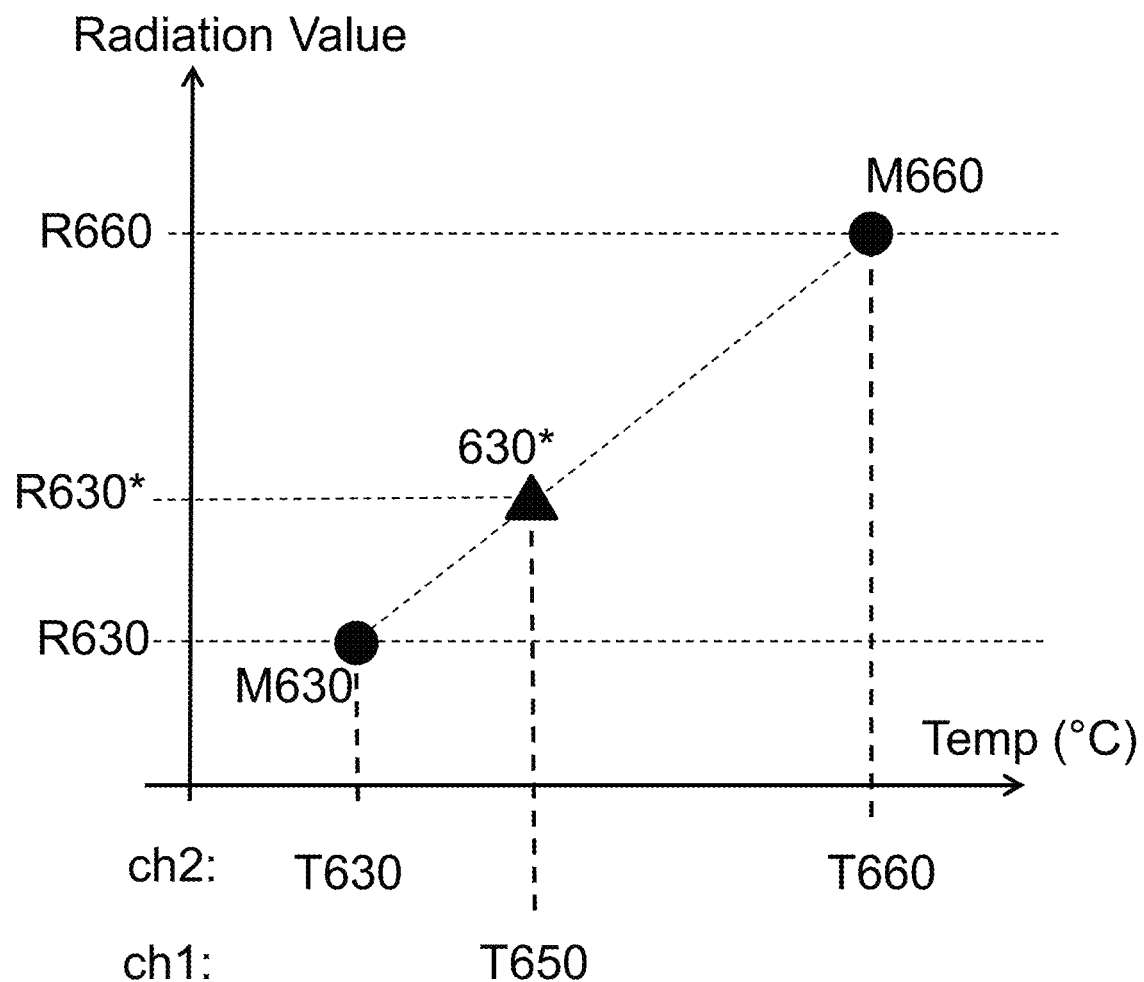

FIG. 19 illustrates the method of the "time shift" in more detail.

Figures 20, 21:
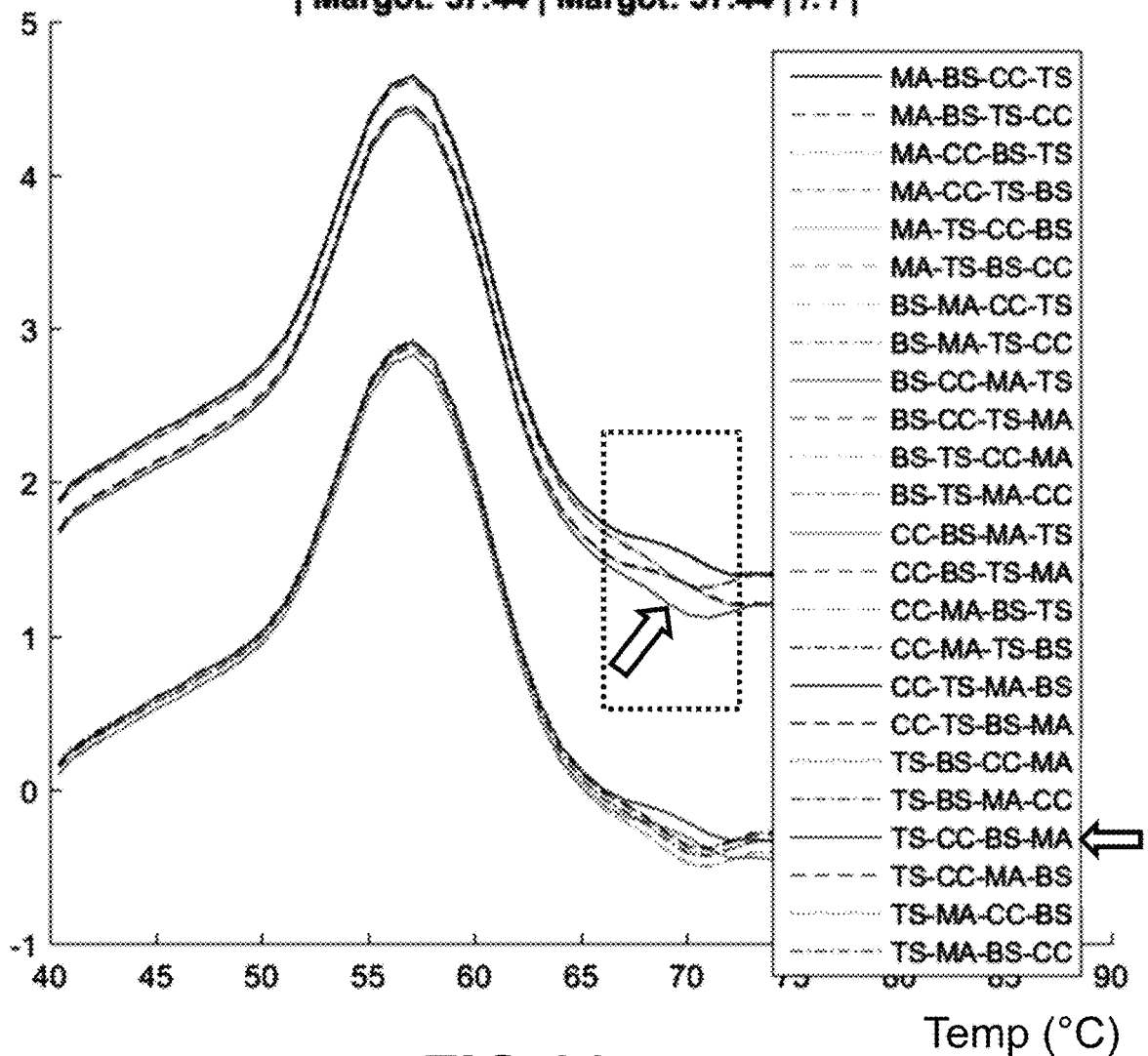

FIG. 20 shows a set of exemplary curves to illustrate that the order of the different steps may have (and sometimes does have) an influence on the detection of a peak or shoulder.

FIG. 21 shows a table with values illustrating the improved accuracy of method according to embodiments of the present disclosure.

Figure 22:
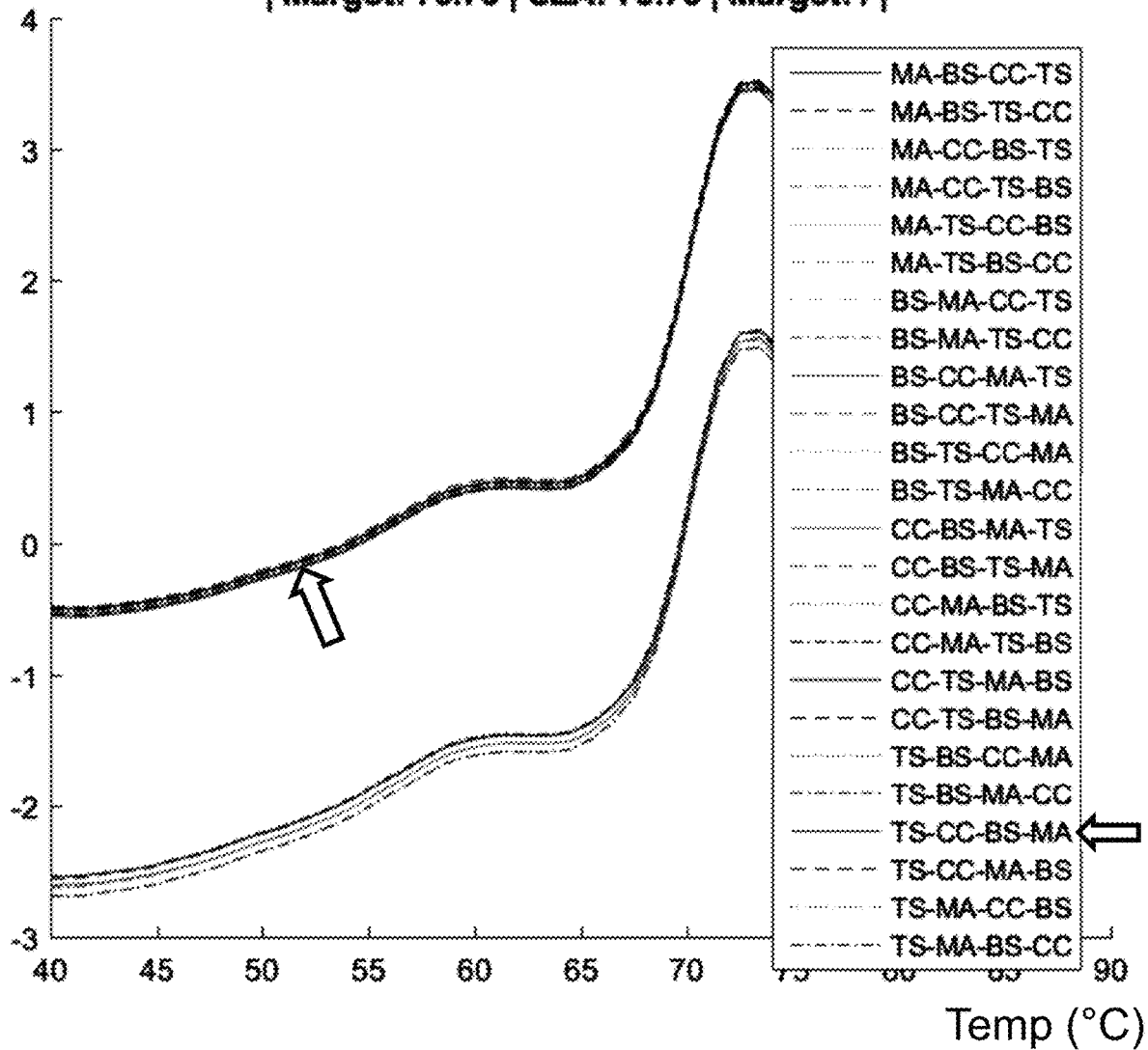

FIG. 22 shows another set of exemplary curves, where the order is less important.

FIG. 23 shows an example of an XML file showing a typical example of how temperature values and radiation values, measured by a real-time PCR device, are provided for further processing.

Figure 24:
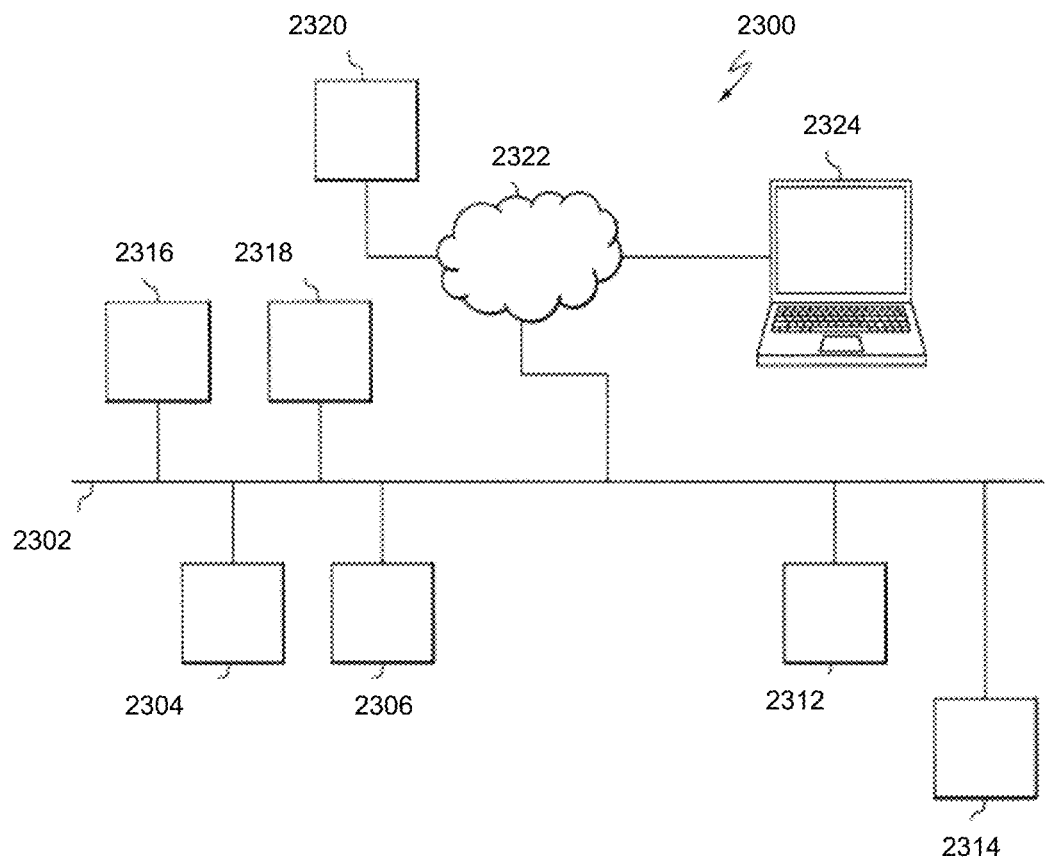

FIG. 24 schematically illustrates a system for implementing computer and software based methods as described herein, according to one or more embodiments shown and described herein.

Where in the following description reference is made to "environmental parameters", reference is made to "temperature", unless mentioned otherwise, or unless clear from the context otherwise.

DETAILED DESCRIPTION

The disclosure includes methods that can at least partially be implemented in software, in particular for use in calculating, correcting and processing data used in bio-technological applications, such as fluorescence in PCR analysis, and as such, it is aimed at applications for detection of target molecules, more specifically infections in the samples to be analyzed.

The below represents a possible embodiment, however, the disclosure is not limited to this embodiment alone. While the disclosure will be described primarily for three fluorescent channels, FAM, ROX, CY5, the present disclosure is not limited to data or systems with three fluorescent channels, but less than 3 or more than 3 channels can also be used, for example only 2 channels, or 4 channels, or 5 channels, or more than 5 channels. Also, while the names FAM, ROX and CY5 are used as particular examples, the present disclosure is not limited thereto, and other fluorescences may also be used.

In FIGS. 2 and 3, the x-axis (10) represents the wavelength of the measured light and the y-axis represents the amount of measured light (fluorescence), also referred to herein as radiation values.

In FIGS. 4 to 10 (here only illustrated in FIG. 4), FIGS. 13 to 15 and FIG. 17, the x-axis (30) represents the temperature (indicative for the environment of the measurement sample) and the y-axis (40) represents processed fluorescence data (for example minus the derivative of those data to the temperature).

Software for Performing Methods According to This Disclosure

In a particular embodiment of the present disclosure, it was decided to develop a standalone software application. This simplifies the use and the installation of the software for the end-user. This way, all data remain on one system, which appears safer when there are many users. The methods according to this disclosure work on data obtained from systems for PCR analysis. Such systems often contain an integrated software package to visualize the measured data. However, these software packages are at first instance aimed at research and development, which is at the same time also the biggest disadvantage. Every time the user wants to view a sample, he needs to perform various actions (mouse clicks) and thus taking some time to retrieve the data, especially if he/she wants to analyze multiple samples. However, from this integrated software it is possible to export data to, for example an XML file. This way, all data related to a certain run are saved in one file. This XML file, or other suitable files (e.g. text files (txt)) are used in the method according to this disclosure and could be captured in the related software. One of the aspects of the disclosure is thus to be able to process data received in various formats.

This way, the user is able to export the data after the full cycle in the PCR device, with only a single mouse click. From there he could use the method of the current disclosure to perform the full data analysis.

In addition to the increased efficiency and accuracy, it is also possible via methods of the present disclosure to lift the technology of the users to a higher level. Modifications made with the method of this disclosure enable users to detect multiple parameters (for example Fluorescence channels) that increase the options of their tests (e.g. multiplex).

Loading the Data

Loading the data in the software to perform the methods according to this disclosure is performed using a completely self-developed code. The XML file that must be loaded consists of 150 000 lines. Since we only want to use some of this information, we filter the desired data from this file. An object is created for every sample and all objects are kept in a list. Every sample object contains the raw fluorescence data (also referred to as "radiation value") and the temperature for the three parameters measured (e.g. FAM, ROX and CY5 channels). The flow chart of the flow diagram represented in FIG. 1 schematically shows the code written to capture all data from the XML file. An exemplary portion of such an XML file is shown in FIG. 23.

Editing the Data

Before we can analyze the data, we must first edit and compensate the data. We perform four steps to edit raw data.
1. Time shift (TS)
2. Colour comp (CC)
3. Subtraction (BS)
4. Moving average (MA)

Time Shift

Time shift correction is one of the first corrections we perform. This correction is required to compare various parameters (fluorescence channels) at the same temperature.

In what follows, prefix "t" is used to indicate "time", prefix "M" is used to indicate "Measurement", prefix "R" is used to indicate "Radiation", and index "T" is used to indicate "Temperature".

The disclosure describes a method for adjusting a subset of measurements (M630, M660, M670) of at least one e.g. a second fluorescence spectrum (600) from multiple parameters, e.g. fluorescence spectra (600, 610, 620), each being subjected to the same time-dependent environment, where the measurements are taken at different time points (t700, t703, t706) and where the adjustments result in calculated values (R630*, R660*, R670*) which can be compared with corresponding measurements (M650, M680, M690) of a first parameter, e.g. fluorescent spectrum (620), as if they were taken at the same temperature.

The measuring hardware will internally continuously increase the temperature during the PCR response. Since various fluorescence channels are measured one after the other, every channel is read at a different temperature (see example in FIG. 23). This way there is a slight change on the temperature scale between the measured fluorescence in, for example the FAM and ROX channels and between the ROX and CY5 channels. (FIG. 2). The time shift correction is performed on the raw data. In the software, the temperatures from the first channels are compensated to the temperature of the last of these channels, for example the FAM and ROX channels are compensated to the temperature of CY5. Through this correction, we are able to compare the measurements received from the various channels at the same temperature. The time shift interpolates the data based on the temperature from the current and the next channel. Depending on the temperature measured in the first channels (for example ROX or FAM), we will compensate more or less. For example, we compensate the FAM and ROX temperature based on the CY5 temperature. This ensures that the corrected data (calculated values) move to a slightly different temperature where the following measurement takes place.

During the development of this time shift correction we assessed, based on the data originating from various exports, how we could optimally do this compensation. Eventually we decided to move the temperatures from the first channels (e.g. FAM and ROX) to the last channel (e.g. CY5). However, it is possible to use any channel as reference and to correct the values from the other channels to this. In a specific embodiment of the software, the time shift correction will be the first correction on the raw data. As, in this specific embodiment, the artificially incorrect reference values (for the environment, for example, represented by the temperature and actually underlying the incorrect reference time) are no longer used in the further steps, these further steps take place more optimally and therefore finally results in an improved detection of target molecules, and, more especially, results in a better detection of the infections in the samples to be analyzed. The insight of this specific embodiment, more specifically that the time correction should take place before the colour compensation, requires that any possible colour compensation on the device should be switched off. This will be explained further.

The time shift correction is performed both on the fluorescence data of the sample to be analyzed and on the data of the negative control. This negative control (reference sample) is a sample that only contains the reagents and no clinical material. Time shift preferably takes place on the data from the first channels (for example the FAM and ROX channel).

FIG. 18 illustrates measurements (dark grey, for example M630), set out along a time axis, for various parameters e.g. fluorescence channels (600, 610, 620), taken at various time points (t700 . . . t708) and calculated measurements (light grey, for example R630*).

In the example of FIG. 18, mathematically, the data are interpolated based on the temperature of the channel 620 (e.g. CY5), with preference according to interpolation on a curve with X and Y values. This will be explained in more detail in FIG. 19.

Colour Compensation

The colour compensation is a very important step in obtaining a correct analysis later.

In a next aspect, the disclosure thus includes a method for modifying fluorescent measurements (300, 310, 320) of a sample, where the measurements are taken in at least two partially overlapping wavelengths, which method then includes steps of: (1) determining fluorescence measurements, (2) determining information indicative for said overlap, (3) adjustment of the fluorescence measurements, by using matrix multiplications and/or mathematical multiplication operations based on the information from step (2), to reduce the influence of said overlapping.

During the real-time PCR process, measurements take place in three channels. This causes a radiation of the signal from the first channel (e.g. the FAM channel) to the second channel (e.g. the ROX channel) and from the second channel (e.g. the ROX channel) to the last channel (e.g. the CY5 channel). This radiation can clearly be seen in FIG. 3. The curve corresponding with the first channel (300) partially overlaps with the curve from the second channel (310). This overlapping part is the radiation (330) of the first channel (FAM) into the second channel (ROX). This also happens with the signal of the second channel (310), which radiates in the curve of the last signal (320). This last radiation (340) is the radiation of the second channel (ROX) into the last channel (CY5).

The percentage radiation of the various channels depends on the device used. In order to perform a correct colour compensation, a calibration must be performed on every device to determine to what extend there is radiation between the various channels. Without this correction, errors could occur during the analysis due to peaks that radiate from one channel into another channel. In order to perform a colour compensation, we must first calculate the correction factors, which we can use later to correct the measured data. We calculate these correction factors based on the data originating from a colour compensation run or calibration run. The software was developed in such a manner that once this run has been captured, the correction factors are stored on the hard disk of the user. The user will from now on be able to reload and use these correction factors every time he opens the software.

In particular embodiments, matrix coefficients are determined during a calibration test, and are stored for later use. Thus, methods for correcting the data can consider these values are being "predefined values".

During the calibration test, colour compensation is performed on the raw data. The correction that is performed depends on a colour compensation run. In such a run, the fluorescence is also measured in the three different channels. The only difference with a normal run is that the samples do not contain all fluorescent labels, but that there are samples with only ROX, CY5 or FAM labels. By radiating and measuring one of the samples in the three channels during the analysis, it is possible to determine the amount of radiation into the other channels. These measurements are only possible when there is only one fluorescent label in the samples.

FIGS. 4 and 5 indicate the purpose of the colour compensation.

Assume we have a peak in ROX as seen in FIG. 4. This peak has a height of approximately 0.7. If we determined via the colour compensation run that the ROX channel radiates 35% into the CY5 channel, we would need to see a peak of approximately 0.25 in the CY5 channel when the colour compensation is turned off. (FIG. 5).

Once we activate the colour compensation, the peak disappears in the CY5 channel. Since there is no longer any radiation, the peak, originating from the radiation of ROX, disappears. We now have a minimum in CY5 that is actually indicative of an over-compensation (FIG. 6). With the over-compensation, an infection in CY5 at the same place as the radiation would also disappear. We optimized the colour compensation algorithm in the software so that there will not be any over-compensation, such that the peaks that are indeed an infection are not mistakenly filtered out.

If we look in more detail into this colour compensation we will compensate the data based on the correction factors. We only need to apply the colour compensation on the second and subsequent channels (e.g. ROX and CY5), because only these channels could have radiation. The first channel measured (e.g. FAM) will not have any radiation from channels with a lower wavelength.

The correction from FAM to ROX is explained first. To compensate the radiation of FAM in the ROX channel, a function is written, which departs from four parameters: the raw fluorescence data from the ROX channel, the possible time shift correcting data from the FAM channel and the radiation percentage of the FAM channel. We will calculate a corrected dataset based on the abovementioned data, which we can use further as corrected data for the ROX channel.

The colour compensation happens based on an algorithm we developed that can be tailor-made for the end-user, which will improve the effect in comparison to the existing algorithms available. In a specific embodiment of the disclosure, the user should therefore switch off any colour compensation present on the device. More concretely, this specific embodiment therefore comprises of establishing a number of measurements each taken at a different time point to that of the first parameter, whereby the measurements are fluorescent data of the real time PCR-experiments, whereby the colour compensation on the device is switched off. In an alternative embodiment of the disclosure, (for example in a case where the user cannot switch off any possible colour compensation present on the device), the method of the disclosure will, besides the necessary colour compensation, also compensate for any aberrant colour compensation of the device.

For the colour compensation, we will measure the radiation for every device once. This happens by loading a specific run on the device. By merely radiating and measuring 1 channel, we will know the amount of radiation. Based on the percentage measured here, we will later be able to correct other runs via multiplication.

Subtraction

Subtraction is a possible third correction that we use. With this subtraction, we want to remove the background of the signal. After subtraction, we only retain the pure data without an artificial increase by a specific background or noise.

This kind of subtraction is known per se in the art, and is typically referred to as "baseline correction".

FIG. 7 shows that the curve for the negative control (400) is not completely on 0, but in this case around 0.1. This signal is the result of a sample with all PCR reagents, but without a DNA sample in the reaction. Theoretically, it will not be possible for any products to form without DNA. Theoretically, it would also not be possible to measure a fluorescence in 1 of the channels of this negative control. If we test this in practice we will clearly see a light background. This background is indicated on the graph as the curve (400). In the corrected graph (FIG. 8) we removed this background by subtracting the negative control signal at the fluorescence data of the sample and the fluorescence data of the negative control. This way, the curve (410) of the negative control is perfectly on 0 for all points. The graph (420) that reflects the fluorescence data of the sample is lower as a result of this subtraction. Depending on the height of the background, the sample data will drop more or less as a result of this subtraction.

Mathematically, the subtraction consists of a difference between the signal and the background.

Moving Average

The moving average is not a correction to rectify measurement errors. However, this moving average was included in the software. After investigation we saw that it was efficient to optimize the data based on this moving average. There were no visible spikes on the raw data, but we saw that the form of the graphs was not always optimal. After further analyzing this problem, we concluded that this was due to the current protocol where only one measurement per 1° C. increase is determined. By compensating the data via the moving average, the deviances from the data disappeared By using a moving average, we were able to "smooth" the graph. We could experimentally conclude that this smoothing would later simplify the detection of target molecules, in particular infections.

The moving average is preferably the last correction of the data. This correction does not take place on the raw data, but on the derivate data. We must always use the derivative data to calculate the gradient of the curve to ensure maximum detection.

FIG. 9 shows the advantage of this correction. In the screenshots we see how the curve in the graph (A) is rather angular, while it is more smooth after correction with the moving average in graph (B). The smoothing of this graph was increased by applying the moving average to the derivative data. This very light maximum, which was present in graph (A) was practically removed in graph (B) due to the smoothing. This proves that peak detection on flowing data is even easier.

Mathematically, a moving average can happen by replacing a point by the average of the point and one or more of the next points.

But the present disclosure is not limited to this particular implementation of moving-average, and other ways of using a "sliding window", or using low pass filter may also be used.

Correction Parameters

In order to perform all corrections, a number of mathematical parameters can be used. This way the extent of the correction can be adjusted experimentally. The correction of the data is important to perform a correct peak detection. The amount of smoothing is a balance between a flowing curve and still maintaining sufficient resolution to in order not to lose small infections from the results.

Dx: this first parameter determines how we calculate the derivative values based on the adjustable parameter 9dx (the differentiation interval). The higher this dx value, the higher the reach of the subtraction and the smoother our curve will be. This value may also not be too high because this could lead to insufficient resolution to perform a correct analysis. A number of points are always lost when deriving the data. In an embodiment, the subtraction of data was designed in such a way that not all data points at the back are lost. For example, assume that we know that the melting point temperature when calculating the first target molecule from the panel is at least 53° C., while the melting point temperature when calculating the last target molecule from the panel is a maximum of 80° C. and we can measure with the measuring equipment between 45° and 85°. From this data we can lose a few data points in the front (low temperature) and at the back (high temperature) without losing useful data pairs.

FIG. 10 shows how the data can be derived. Since we can view the gradient between dx points left and right from a measuring point we lose dx points at the front and in the back (see respectively (800, 810). This way we are able to properly derive without losing any data points close to the values with regard to the first or last target molecule.

Moving Average DX: Moving average can, as described before, be used to compensate the minor irregularities in the curve. This creates a smoother curve that simplifies peak detection. By this correction, the number of maxima reduces. We filter out the maxima, which do not correspond with a target molecule.

Here too, we work in such a manner that we lose a point in the front and at the back. The principle is identical to the manner in which we derive. Assume a dx of 1 is used for the moving average, the average will be calculated based on 1 point in front and one point behind the current point and the point itself. If a dx of 0 is chosen for the moving average, the part between the current and the next point will be taken into consideration. This way we only lose one point at the back.

In an embodiment, a limited subtraction is combined with a moving average. Both mathematical operations will smoothen the curve to some extent.

Extra percentage colour compensation: It is possible to increase a percentage of the correction factors for the colour compensation in the software. This way, the user can increase the influence of the colour. In certain cases, this could lead to an improved correction.

Apart from the option to set the quantity of correction for the various corrections, it is possible to eliminate one or more corrections individually. The software was developed in such a manner that every compensation can be included or excluded separately, while only the other corrections will continue to happen correctly.

Conclusion Processing of the Data

FIG. 11 shows the full flowchart of the function, which will correct the data. The function requires a sample number and a channel as parameters. Based on these data, the correct data are calculated for the desired sample and the selected channel and the curve are displayed. The flow of this algorithm was established by experimentally starting to search for the most suitable manner to correct this data. Apart from the various methods to correct the data, we also looked into the sequence in which the various steps could be taken. We had to determine the parameters for the various corrections, which led to a search for the correct balance between smoothing and a good correction, which will not lead to any loss of data.

FIG. 11 shows in step (100) how to determine the calculated values, for the parameter which measures are loaded (fluorescence channel), by using these loaded measurements, to achieve the calculated values, representative for the parameter under the environment at the loaded time. FIG. 11 shows in step (200) the adjustment of the aforementioned calculated value to suppress the influence of the frequency overlap by using the loaded information. FIG. 11 shows in step (300) how to determine the presence of background signals for at least one of the parameters; and correcting (subtracting) the adjusted measurements. FIG. 11 shows in step (400) the smoothing, preferably through a moving average, of the calculated values. FIG. 11 also shows the preferred sequence of the sub methods and steps.

Validation of Negative Control

Before we start analyzing the data, we check the IAC (internal amplification control). By checking the IAC we can determine whether the reaction in the kit occurred correctly. Depending on the kit, there is a temperature at which the IAC signal must have a minimum if no infections are found in the ROX or CY5 channel. We have included a few parameters for the validation of the IAC. When we tested the software, we established that certain weak infections were not detected. After analyzing these specific cases, we came to the decision that it was not the parameters that had to be adjusted, but that a better negative balance ensured that we could realize better normalization which meant that the weak infections that would have been missed earlier, came to the surface. When the user choose to validate the IAC, he receives a notification with the option to implement a new IAC if the previously entered IAC does not comply with the requirements of the valid IAC. If the user gives the same IAC as before or the current IAC, the software will use this IAC. A valid IAC is a valid negative signal with sufficient difference between the first and last fluorescence value. See FIG. 12.

Data Analysis

After all data are accurately corrected, the data will be analyzed. This analysis consists of filtering the infection peaks from the full data set. As seen from FIG. 13, not all maxima are truly the maximum for a certain infection. This then also illustrates the inventive contribution of the disclosure. There is an enormous variety of data, but the algorithm must process the data universally and always only filter the correct maxima from the full data set. In order to do this, we developed a set of functions that analyze the data set or a portion of this data set. From the moment when a maximum successfully passes this analysis one could conclude that the maximum represents a certain infection.

We divided the analysis of single infections and multiple infections. This way an infection is always scored at its absolute maximum. This way there is never a possibility that we can miss even the most obvious infection from multiple infection. From the moment when this maximum complies with a combination of parameters there will be a further investigation as to see whether there is shoulder to the left or right of the maximum found.

In certain cases we are not dealing with a shoulder infection, but with a multiple infection that can be identified by its enormous width at the bottom. We must also perform an analysis of these infections, which can only be performed in the cases that we can derive from the data whether this is potentially a multiple infection. FIG. 14 clearly shows this. A clear shoulder can be seen. To the left of the scored infection there is a smaller, weaker infection that ensures that the curve obtains a certain shoulder. FIG. 15 shows a clear example of a multiple infection without a shoulder.

The major difference between both curves lies in the symmetry of the curve. A multiple infection without a shoulder will always to a large extent be symmetric with regard to the vertical symmetry lines due to the maximum found. In contrast to this, a shoulder infection will be symmetrical at the top but always asymmetrical at shoulder height. Based on this symmetry calculation, we also search for multiple infections or shoulder infections.

From a general point of view the discovered method thus enables, based on the aforementioned adjusted measurements, the detection of the presence of the aforementioned contamination, by determining the maxima and by classifying the contamination by performing a symmetry analysis on the aforementioned adjusted measurements concerning the specified maximum.

During the analysis we have used a lot of parameters to filter the infection peaks from the full data set.

Thus, as indicated earlier, the ability to set parameters of the methods and the underlying software contribute to the disclosure. The various parameters that could be used are discussed in more detail below.

Dynamic factor threshold positive: Determines how many times the threshold for clearly positive infections lies higher than the average value of the negative control. For example, the average value of the negative control is 0.1 and the Dynamic factor threshold positive is 2.5, then the peak must be higher than 0.25 to be considered as clearly positive.

Dynamic factor Threshold Negative: Identical to the previous parameter. This value will only determine the minimum threshold for the uncertain area. An infection that is higher than this threshold but still lower than the positive threshold falls in the uncertain area. This uncertain area is a zone that includes the uncertain cases. The user should rather once again, visually check the infections from this uncertain area.

Absolute factor raw: In order to consider a signal as an infection, there must be an absolute difference between the sample data and the negative control that is higher than this parameter. The difference here always concerns the raw data and the first point from both data sets. The difference occurs based on the fluorescence of the sample and the fluorescence of the negative control.

Dynamic factor raw: A signal can only be scored as an infection when the first data point is higher than the measurement of the negative control multiplied by this parameter. Here too, the raw fluorescence data is used for the calculation.

Width: This parameter contains the minimum width that an infection peak must have. The distance from the top used to look at the width is determined by the PercentageWidth parameter.

Percentage width: This parameter gives the percentage from where the width must be viewed. This percentage is always seen from the top. Assume we have a maximum with a Y value of 1 and this percentage is set at 15%, then the width of the peak will be viewed from a height of 0.85. This way, an infection must have a certain width and height, something that lots of maxima do not have and that can be found at infection peaks. Based on this and the previous parameter, we filter quite a lot of incorrect maxima from the area around the background.

Width Bottom & Percentage bottom border: These parameters work identical to the normal width and the related percentage. These parameters will only be used to view the width at the bottom. These parameters play an important role in the detection of multiple infections without a shoulder. Since these peaks are characterized by an enormous width at the bottom, they are easy to detect based on these values.

Absolute threshold: This threshold is an absolute threshold. A peak must always be higher than this value to be seen as an infection. Even if the peak is still above the dynamic threshold, but still not higher than this value it will not be a valid infection peak. This parameter was created to filter maxima in the background. In certain situations we found maxima in negative signals that were still scored as infections.

Double infection peak minimum height: this parameter is identical to the abovementioned parameter and this parameter will record a minimum height for double infections.

Symmetry difference left right: In order to detect shoulders, we view the symmetry at a certain height. A shoulder must have a deviation from the symmetry that is higher than this value to be able to be scored as a shoulder. This deviation is calculated based on the ratio between the left and right part of the symmetry axis. When a signal has to deviate 30%, i.e. that the ratio between the left part of the symmetry axis and the right part must be lower than 0.7 or higher than 1.3.

Symmetry height: The height at which the symmetry axis is viewed depends on this percentage. Here too there will be a certain percentage drop from the Y-value. If we view the peak detection in detail in a particular embodiment, the flow diagram of FIG. 16 can be followed. As you can see, we first detect every maximum applicable to one or more infections. From the moment a maximum has been detected, we will further analyze whether this maximum is single or multiple.

Automatic Detection of Samples

Before starting the analysis, the software must preferably first check which sample has been identified as negative control. The user can specify tags in the software, which can be used to automatically search for negative controls or to differentiate a mix1 and mix2 sample. When the user submits his tags once, these are saved on the hard disk of the system and these will always be loaded when the user starts the software.

When we evaluated the data analysis and compared it with prior art software we see that the data analysis of the disclosure is similar in 90% of the cases for all compared software packages. The difference between the software packages lies in the other 10%. This last 10% of the peaks include the very weak infections, the shoulders and the multiple infections. Because this concerns medical diagnostics, the software score must be trusted for 100%. When only 2% of the cases cannot be scored accurately, all samples must be checked visually to ensure that the score was correct.

In order to solve this problem, a negative, uncertain and certain positive zone is used in an embodiment of the disclosure. The parameter setting must be determined in such a manner that we are certain that a peak is positive at a result in the green or positive area. The situations where the peak lands in the uncertain area must still be checked visually by the user. This way the number of samples that must be analyzed manually are reduced to the number that falls in the orange zone. This way we also do not score any false positives. FIG. 17 shows the zones with the accompanying result. The disclosure is unique in the use of more than 2 zones, preferably 3 zones (500 positive, 510 uncertain, 520 negative). This approach is consciously chosen because this will lead to the realization of a more reliable result.

In general the methods thus detect, based on the aforementioned adjusted measurements, the presence of said contamination, preferably by determining the maximum and by including a 3-value-score of the reliability of this determination.

Output of the Data

After a correction and analysis was performed on the data, it must also be possible to export the data. By creating an export, the user gets a nice global overview with the results of the complete run.

The software also offers the opportunity to give an overview of the infections found for a certain sample in the software with accompanying curves for the selected channel. If the user wants to automatically score the full run, he should rather select an export. This export will always be created by the software as a PDF and CSV file. The CSV gives the opportunity to easily process the data in spreadsheets such as Excel. The export of the PDF has, depending on the mode where the PDF is created, a different layout. In the software, we differentiate the experimental mode where it is possible to compare 2 parameter settings with one another and the mode to score infections. A second mode is the mode to score peak names. This mode was developed to automatically score a run and to quickly receive a summary with the various samples and the infections found. In this mode a summary is created internally, in the software, between a 1 mix assay and 2 mix assays. It is necessary that both samples have the same name, with a specific tag at the end that indicates whether it concerns a mix1 or mix2. A pdf of a 2 mix assay in the "score peak names" mixes always next to each other with the infections found and the accompanying data below the curves. For the user, nothing changes about the software. The user chooses the assay he wants to use. Depending on the assay used, the software processes the export in a different manner. This happens without any interference of the user. On the background there is a clear difference though between the processing of a 2-mix assay and a 1-mix assay. In the 2-mix mode, 1 sample will also be displayed per page. If only 1 of the mixes had to be included in the run for a certain sample, the software will indicate this by leaving the column to the left or right of the corresponding mix empty. At a "Score peak Name" export, the PDF contains a table with a summary of the results on the first page. This way it is easy to quickly obtain a global summary of the full run. After this summary there will be a table with the parameters used during the run.

In FIG. 19, the time-shift correction is shown in more detail. The X-axis corresponds to the temperature, and the Y-axis corresponds to the radiation value of a particular fluorescent channel. The point M630 represents a measurement where a radiation value R630 and a temperature T630 are measured at a certain moment t700 in time (see FIG. 18, but not shown in FIG. 19), and the point M660 represents a measurement where radiation value R660 and temperature T660 are measured at another moment t730 in time (see FIG. 18, but not shown in FIG. 19). The black triangle represents the estimated radiation value R630° which would be measured if the sample would have had a temperature equal to T650, which is the temperature measured at time t720 (see FIG. 18) in another fluorescent channel, which occurs after the measurement M630 was taken, but before the measurement M660 was taken.

Referring back to FIG. 18, one of the underlying ideas of the present disclosure is that the color correction step is not performed using the measured values R630 and R640 and R650 (in case of three fluorescent channels), but instead using estimated values which would have been measured if all measurements would have been taken at a same temperature (in the example: T650).

FIG. 20 shows a set of exemplary curves to illustrate that the order of the different steps may have (and sometimes does have) an influence on the detection of a peak or shoulder. In the particular example shown, the curve indicated by the arrow is calculated using the "TS-CC-BS-MA" order, (meaning first Time-Shift, then Color Correction, then BaSeline-correction, and then Moving Average). Although the differences between the curves may seem subtle, the consequences may be huge. The main contribution of the present disclosure is exactly when these subtle differences give rise to ambiguity. The question to be answered is, whether a peak or shoulder is present in the area indicated by the dotted line, or not, and depending on the outcome, a different clinical decision will be taken. As shown, different orders of the steps provide a slight "bump" in the curve, which may be mis-interpreted as the presence of a peak or shoulder. However, the order proposed by the present disclosure, does not introduce such errors. This figure shows that it is paramount to provide data which is as accurate as possible, in order to avoid false interpretation of the results.

FIG. 21 shows a table with values illustrating the improved accuracy of method according to embodiments of the present disclosure. As can be seen, the order "TS-CC-BS-MA" provides the best results. The interested reader may wonder whether the order "BS-TS-CC-MA" and "TS-BS-CC-MA" are also good enough. The difference is that about 1 person out of 100 persons is falsely diagnosed as having a particular disease, for example cancer, and is treated accordingly. Statistically this may not seem like a huge difference, but in terms of human suffering of the particular individual, this is a huge difference.

FIG. 22 shows another set of exemplary curves, where the order is less important. (this happens in 90% of the cases).

FIG. 23 shows an example of an XML file showing a typical example of how temperature values and radiation values, measured by a real-time PCR device, are provided for further processing. as can be seen, this particular real-time PCR device provides for each measurement three values: a radiation value, a temperature value and a time value.

Referring to FIG. 24, a system 2300 for implementing a computer and software-based methods such as software algorithms as described herein is illustrated as being implemented along with using a graphical user interface (GUI) as a display that is accessible at a user workstation (e.g., a computer 2324), for example. The system 2300 includes a communication path 2302, one or more processors 2304, a memory component 2306, an interpolation component 2312 to interpolate values as described herein, a storage or database 2314, a measurement component 2316 to measure values as described herein, a network interface hardware 2318, a network 2322, a server 2320, and at least one computer 2324. The various components of the system 2300 and the interaction thereof will be described in detail below.

In some embodiments, the system 2300 is implemented using a wide area network (WAN) or network 2322, such as an intranet or the Internet, or other wired or wireless communication network that may include a cloud computing-based network configuration. The workstation computer 2324 may include digital systems and other devices permitting connection to and navigation of the network. Other system 2300 variations allowing for communication between various geographically diverse components are possible. The lines depicted in FIG. 24 indicate communication rather than physical connections between the various components.

As noted above, the system 2300 includes the communication path 2302. The communication path 2302 may be formed from any medium that is capable of transmitting a signal such as, for example, conductive wires, conductive traces, optical waveguides, or the like, or from a combination of mediums capable of transmitting signals. The communication path 2302 communicatively couples the various components of the system 2300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 2300 includes the processor 2304. The processor 2304 can be any device capable of executing machine readable instructions. Accordingly, the processor 2304 may be a controller, an integrated circuit, a microchip, a computer, or any other computing device. The processor 2304 is communicatively coupled to the other components of the system 2300 by the communication path 2302. Accordingly, the communication path 2302 may communicatively couple any number of processors with one another, and allow the modules coupled to the communication path 2302 to operate in a distributed computing environment. Specifically, each of the modules can operate as a node that may send and/or receive data.

As noted above, the system 2300 includes the memory component 2306 which is coupled to the communication path 2302 and communicatively coupled to the processor 2304. The memory component 2306 may be a non-transitory computer readable medium or non-transitory computer readable memory and may be configured as a nonvolatile computer readable medium. The memory component 2306 may comprise RAM, ROM, flash memories, hard drives, or any device capable of storing machine readable instructions such that the machine readable instructions can be accessed and executed by the processor 2304. The machine readable instructions may comprise logic or algorithm(s), such as software algorithms as described herein, written in any programming language such as, for example, machine language that may be directly executed by the processor, or assembly language, object-oriented programming (OOP), scripting languages, microcode, etc., that may be compiled or assembled into machine readable instructions and stored on the memory component 2306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 2300 may include the processor 2304 communicatively coupled to the memory component 2306 that stores instructions that, when executed by the processor, cause the processor to perform one or more tool functions such as machine readable instructions execution as described herein.

Still referring to FIG. 24, as noted above, the system 300 comprises the display such as a GUI on a screen of the computer 2324 for providing visual output such as, for example, information, graphical reports, messages, or a combination thereof. The computer 2324 may include one or more computing devices across platforms, or may be communicatively coupled to devices across platforms, such as mobile smart devices including smartphones, tablets, laptops, and/or the like. The display on the screen of the computer 2324 is coupled to the communication path 2302 and communicatively coupled to the processor 2304. Accordingly, the communication path 2302 communicatively couples the display to other modules of the system 2300. The display can include any medium capable of transmitting an optical output such as, for example, a cathode ray tube, light emitting diodes, a liquid crystal display, a plasma display, or the like. Additionally, it is noted that the display or the computer 2324 can include at least one of the processor 2304 and the memory component 2306. While the system 2300 is illustrated as a single, integrated system in FIG. 24, in other embodiments, the systems can be independent systems.

The system 2300 includes the network interface hardware 2318 for communicatively coupling the system 2300 with a computer network such as network 2322. The network interface hardware 2318 is coupled to the communication path 302 such that the communication path 2302 communicatively couples the network interface hardware 2318 to other modules of the system 2300. The network interface hardware 2318 can be any device capable of transmitting and/or receiving data via a wireless network. Accordingly, the network interface hardware 2318 can include a communication transceiver for sending and/or receiving data according to any wireless communication standard. For example, the network interface hardware 2318 can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 24, data from various applications running on computer 2324 can be provided from the computer 2324 to the system 2300 via the network interface hardware 2318. The computer 2324 can be any device having hardware (e.g., chipsets, processors, memory, etc.) for communicatively coupling with the network interface hardware 2318 and a network 2322. Specifically, the computer 2324 can include an input device having an antenna for communicating over one or more of the wireless computer networks described above.

The network 2322 can include any wired and/or wireless network such as, for example, wide area networks, metropolitan area networks, the Internet, an Intranet, satellite networks, or the like. Accordingly, the network 2322 can be utilized as a wireless access point by the computer 2324 to access one or more servers (e.g., a server 2320). The server 2320 and any additional servers generally include processors, memory, and chipset for delivering resources via the network 2322. Resources can include providing, for example, processing, storage, software, and information from the server 2320 to the system 2300 via the network 2322. Additionally, it is noted that the server 2320 and any additional servers can share resources with one another over the network 2322 such as, for example, via the wired portion of the network, the wireless portion of the network, or combinations thereof.

For the purposes of describing and defining the present disclosure, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed disclosure or to imply that certain features are critical, essential, or even important to the structure or function of the claimed disclosure. Rather, these terms are merely intended to identify particular aspects of an embodiment of the present disclosure or to emphasize alternative or additional features that may or may not be utilized in a particular embodiment of the present disclosure.

For the purposes of describing and defining the present disclosure it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. Method of capturing and processing real-time polymerase chain reaction (PCR) data related to a sample to be analyzed, the method comprising the steps of:
    a) providing a real-time PCR device capable of capturing multispectral fluorescence data indicative of at least two fluorescence channels having partially overlapping frequency spectra;
    b) measuring a plurality of fluorescence melting curve data of real-time PCR-experiments of said sample using said PCR device, by performing the following steps multiple times, while increasing a temperature at the sample:
        i) at each of one or more first moments in time measuring a respective first temperature value and measuring a respective first radiation value corresponding to a first channel of said at least two fluorescence channels; and
        ii) at each of one or more second moments in time different from the one or more first moments in time, measuring a respective second temperature value and a respective second radiation value corresponding to a second channel of said at least two fluorescence channels, different from the first channel;
    c) storing the plurality of measured first and second temperature values and first and second radiation values respectively corresponding to the one or more first moments in time associated with the first channel and the one or more second moments in time associated with the second channel;
    d) determining a plurality of time-shifted second radiation values by linearly interpolating between two measured second radiation values associated with the second channel, using weighting factors defined by the corresponding measured temperature values comprising the two corresponding measured temperature values associated with the second channel and a corresponding first measured temperature value associated with the first channel disposed between the two corresponding measured temperature values associated with the second channel; and
    e) after performing step d), calculating color corrected first radiation values and calculating color corrected second radiation values, each based on the plurality of the first radiation values and based on the plurality of the time-shifted second radiation values, using predefined coefficients and matrix multiplication, wherein the color corrected first and second radiation values are representative of associated first channel and second channel color determinations to reduce an influence of said partially overlapping frequency spectra between the first channel and the second channel.

2. The method according to claim 1,
    wherein step d) further comprises determining the time-shifted second radiation values R630\*, R660\* according to the following formulas or equivalent formulas:

$R630^* = m^*(T650-T630)+R630$, where $m = (R660-R630)/(T660-T630)$, where T650 is a temperature measurement of the first channel, R630 and T630 are a radiation value and an associated temperature value of a corresponding measurement of the second channel taken before the measurement of the first channel, and R660 and T660 are a radiation value and an associated temperature value of a corresponding measurement of the second channel taken after the temperature measurement T650 of the first channel.

3. The method according to claim 1,
wherein the real-time PCR device is capable of capturing multispectral fluorescence data indicative of at least three fluorescence channels having a partial spectral overlap,
and wherein step b) further comprises:
   iii) at each of one or more third moments in time different from the one or more first and second moments in time, measuring a respective third temperature value and a respective third radiation value corresponding to a third channel of said at least three fluorescence channels, different from the first and second fluorescence channels;
wherein step d) further comprises: determining time-shifted third radiation values by linearly interpolating between two measured third radiation values associated with the third channel, using weighting factors defined by the corresponding measured temperature values comprising the two corresponding measured temperature values associated with the third channel and a corresponding first measured temperature value associated with the first channel disposed between the two corresponding measured temperature values associated with the third channel.

4. The method according to claim 3,
wherein step d) further comprises determining the time-shifted third radiation value of the third channel according to the following formulas or equivalent formulas:

$$R640^* = m^*(T650-T640) + R640, \text{ where}$$

$$m = (R665-R640)/(T665-T640),$$

where T650 is a temperature measurement of the first channel, R640 and T640 are a radiation value and a temperature value of a corresponding measurement of the third channel taken before the measurement of the first channel, and R665 and T665 are a radiation value and a temperature value of a corresponding measurement of the third channel taken after the temperature measurement T650 of the first channel.

5. The method according to claim 1, further comprising the step of:
   f) when said real-time PCR device comprises a color compensation function, disabling the color compensation function of said real-time PCR device, said color compensation function adapted for reducing cross-talk between said at least two fluorescence channels.

6. The method according to claim 1,
further comprising step f) determining a first background signal for the first color corrected values, and subtracting the determined first background signal from the first color corrected values to obtain first baseline corrected values, and
determining a second background signal for the second color corrected values, and subtracting the determined second background signal from the second color corrected values to obtain second baseline corrected values.

7. The method according to claim 1, further comprising the step of f) smoothing or low pass filtering, the baseline corrected values.

8. The method according to claim 7,
further comprising the step of g) calculating a derivative of the baseline-corrected values versus temperature, thereby obtaining derivative data for each of the fluorescence channels;
and further comprising the step of h) finding one or more local peaks or local shoulders in the derivative data;
and/or further comprising the step of presenting this derivative data on a graphics display device.

9. The method according to claim 8,
further comprising the step of: i) determining a presence or absence of one or more target molecules based on the derivative data.

10. A real-time polymerase chain reaction (PCR) device configured for performing the steps of:
   a) providing a real-time PCR device capable of capturing multispectral fluorescence data indicative of at least two fluorescence channels having partially overlapping frequency spectra;
   b) measuring a plurality of fluorescence melting curve data of real-time PCR-experiments of a sample using said PCR device, by performing the following steps multiple times, while increasing a temperature at the sample:
      i) at each of one or more first moments in time measuring a respective first temperature value and measuring a respective first radiation value corresponding to a first channel of said at least two fluorescence channels; and
      ii) at one or more second moments in time different from the one or more first moments in time, measuring a respective second temperature value and a respective second radiation value corresponding to a second channel of said at least two fluorescence channels, different from the first channel;
   c) storing the plurality of measured first and second temperature values and first and second radiation values respectively corresponding to the one or more first moments in time associated with the first channel and the one or more second moments in time associated with the second channel;
   d) determining a plurality of time-shifted second radiation values by linearly interpolating between two measured second radiation values associated with the second channel, using weighting factors defined by the corresponding measured temperature values comprising the two corresponding measured temperature values associated with the second channel and a corresponding first measured temperature value associated with the first channel disposed between the two corresponding measured temperature values associated with the second channel; and
   e) after performing step d), calculating color corrected first radiation values and calculating color corrected second radiation values, each based on the plurality of the first radiation values and based on the plurality of the time-shifted second radiation values, using pre-defined coefficients and matrix multiplication, wherein the color corrected first and second radiation values are representative of associated first channel and second channel color determinations to reduce an influence of said partially overlapping frequency spectra between the first channel and the second channel.

11. A computer program product containing executable instructions stored in a non-transitory memory in communication with a processor of a computer device communicatively coupled to a display device, which instructions cause the computer program product to perform when executed by the processor at least the following:
  a) receiving a plurality of fluorescence melting curve data of real-time polymerase chain reaction (PCR)-experiments of said sample performed by a real-time PCR device capable of capturing multispectral fluorescence data indicative of at least two fluorescence channels having partially overlapping frequency spectra, and which is configured to perform the following steps multiple times, while increasing a temperature at the sample:
    i) at each of one or more first moments in time measuring a respective first temperature value and measuring a respective first radiation value corresponding to a first channel of said at least two fluorescence channels; and
    ii) at each of one or more second moments in time different from the one or more first moments in time, measuring a respective second temperature value and a respective second radiation value corresponding to a second channel of said at least two fluorescence channels, different from the first channel;
  b) storing the plurality of measured first and second temperature values and first and second radiation values respectively corresponding to the one or more first moments in time associated with the first channel and the one or more second moments in time associated with the second channel;
  c) determining a plurality of time-shifted second radiation values by linearly interpolating between two measured second radiation values associated with the second channel, using weighting factors defined by the corresponding measured temperature values comprising the two corresponding measured temperature values associated with the second channel and a corresponding first measured temperature value associated with the first channel disposed between the two corresponding measured temperature values associated with the second channel; and
  d) after performing step c), calculating color corrected first radiation values and calculating color corrected second radiation values, each based on the plurality of the first radiation values and based on the plurality of the time-shifted second radiation values, using predefined coefficients and matrix multiplication, wherein the color corrected first and second radiation values are representative of associated first channel and second channel color determinations to reduce an influence of said partially overlapping frequency spectra between the first channel and the second channel.

12. A computer-implemented method of processing real-time polymerase chain reaction (PCR) data, the method comprising the steps of:
  a) loading a file comprising a plurality of sample objects obtained from systems for PCR analysis, each sample object containing measured raw fluorescence data and measured temperature data for at least two fluorescence channels having partially overlapping frequency spectra;
  the plurality of sample objects being captured and measured in a device one after the other while a temperature is continually increased, wherein the at least two fluorescence channels are subjected to a same time-dependent environment;
  the plurality of sample objects comprising a plurality of first sample objects related to a first fluorescence channel, each first sample object containing first fluorescent data and first temperature data measured at respective first moments in time, and a plurality of second sample objects related to a second fluorescence channel, each second sample object containing second fluorescent data and second temperature data measured at second moments in time different from the first moments in time,
  b) determining a plurality of first time-shifted fluorescent values by interpolating the first fluorescent data with respect to time or with respect to temperature, as if the plurality of first sample objects were measured at the second moments in time or at a temperature equal to the second temperature data; and
  c) after performing step b), calculating first color corrected fluorescent data and second color corrected fluorescent data by using mathematical multiplication operations on the first time-shifted fluorescent data and the second fluorescent data, to reduce an influence of said partially overlapping frequency spectra.

13. The computer-implemented method according to claim 12, further comprising the steps of:
  d) determining presence of background signals for at least one of the fluorescence channels; and
  e) correcting the color corrected measurements for the background signals.

14. The computer-implemented method according to claim 12, further comprising the step of: d) smoothing, smoothing through a moving average, or combinations thereof, of the color corrected measurements.

15. The computer-implemented method claim 12, further comprising the step of: d) determining a presence or absence of one or more target molecules based on the color corrected measurement data.

16. The computer-implemented method according to claim 15, where determining the presence or absence of the one or more target molecules is performed by calculating a maximum and including a 3-value-score for reliability of the determination.

17. The computer-implemented method according to claim 15, further including: e) performing a symmetrical analysis on the corrected measurements.

* * * * *

UNITED STATES PATENT AND TRADEMARK OFFICE
CERTIFICATE OF CORRECTION

PATENT NO. : 11,094,396 B2
APPLICATION NO. : 16/138386
DATED : August 17, 2021
INVENTOR(S) : Uten et al.

It is certified that error appears in the above-identified patent and that said Letters Patent is hereby corrected as shown below:

On the Title Page

Item (74), attorney, agent, or firm, delete "Dinsmore & Shohl, LLP" and insert --Dinsmore & Shohl LLP--, therefor.

Page 2, Column 2, item (56), other publications, Line 11, delete "RealMultiplex" and insert --Real-Time Multiplex--, therefor.

In the Specification

In Column 3, Line(s) 6 & 7, delete "$\begin{cases} R630 \mathrel{*}= m * (T650 - T630), \text{ and} \\ m = (R660 - R630)/(T660 - T630) \end{cases}$," and insert --$\begin{cases} R630 \mathrel{*}= m * (T650 - T630), \text{ and} \\ m = (R660 - R630)/(T660 - T630), \end{cases}$--, therefor.

In Column 3, Line(s) 54 & 55, delete "$\begin{cases} R640 \mathrel{*}= m * (T650 - T640), \text{ where} \\ m = (R665 - R640)/(T665 - T640) \end{cases}$," and insert --$\begin{cases} R640 \mathrel{*}= m * (T650 - T640), \text{ where} \\ m = (R665 - R640)/(T665 - T640), \end{cases}$--, therefor.

In Column 5, Line(s) 34 & 35, delete "$\begin{cases} R630 \mathrel{*}= m * (T650 - T630), \text{ where} \\ m = (R660 - R630)/(T660 - T630) \end{cases}$," and insert Signed and Sealed this
Third Day of May, 2022

*Katherine Kelly Vidal*

Katherine Kelly Vidal
*Director of the United States Patent and Trademark Office*

CERTIFICATE OF CORRECTION (continued)
U.S. Pat. No. 11,094,396 B2

In Column 5, Line(s) 64 & 65, delete "$\begin{cases} R640 *= m*(T650-T640), \text{where} \\ m = (R665-R640)/(T665-T640) \end{cases}$," and insert --$\begin{cases} R640 *= m*(T650-T640), \text{where} \\ m = (R665-R640)/(T665-T640), \end{cases}$--, therefor.

In the Claims

In Column 26, Line(s) 46, Claim 15, after "method", insert --according to--.